(12) United States Patent
Cheng et al.

(10) Patent No.: US 6,727,352 B2
(45) Date of Patent: Apr. 27, 2004

(54) METHODS OF MAKING MACROLIDES

(75) Inventors: Hengmiao Cheng, East Lyme, CT (US); Chao Li, East Lyme, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/226,760

(22) Filed: Aug. 23, 2002

(65) Prior Publication Data

US 2003/0109463 A1 Jun. 12, 2003

Related U.S. Application Data

(62) Division of application No. 09/715,394, filed on Nov. 17, 2000, now Pat. No. 6,518,251.
(60) Provisional application No. 60/166,269, filed on Nov. 18, 1999.

(51) Int. Cl.$^7$ .................................................. C07H 1/00

(52) U.S. Cl. ...................................... 536/7.4; 536/18.5

(58) Field of Search ................................. 536/7.4, 18.5

(56) References Cited

U.S. PATENT DOCUMENTS

| 4,474,768 A | 10/1984 | Bright .......................... 424/180 |
| 4,517,359 A | 5/1985 | Kobrehel et al. ............. 536/7.4 |
| 6,043,227 A | 3/2000 | Cheng et al. .................. 514/29 |

FOREIGN PATENT DOCUMENTS

| WO | WO9801546 | 1/1998 | ........... C12N/15/00 |
| WO | WO9801571 | 1/1998 | ........... C12N/15/62 |
| WO | WO9809978 | 3/1998 | ........... C07H/17/08 |

OTHER PUBLICATIONS

Waddell, et al., Bioorganic & Medicinal Chemistry Letters, 8, 1998, 1321–1326.
Fleisher, et al., Advanced Drug Delivery Reviews, 19, 1996, 115–130.
Robinson et al., Journal of Medicinal Chemistry, 1996, vol. 39., No. 1, 10–18.
Sutcliffe, et al., Antimicrobial Agents and Chemotherapy, Nov. 1996, 2562–2566, vol. 40, No. 11.

*Primary Examiner*—Elli Peselev
(74) *Attorney, Agent, or Firm*—Peter C. Richardson; Gregg C. Benson; D. Timothy Creagon

(57) ABSTRACT

This invention relates to methods of preparing a compound of Formulae 2, 5 and 7, wherein $R^2$–$R^5$, $R^7$, $R^9$, $R^{10}$ and $R^{15}$ are defined herein.

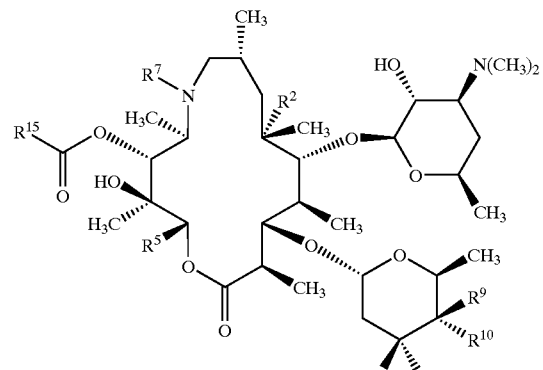

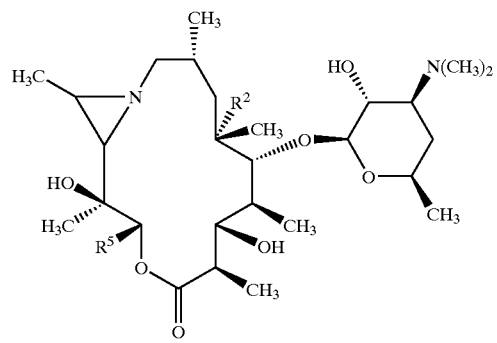

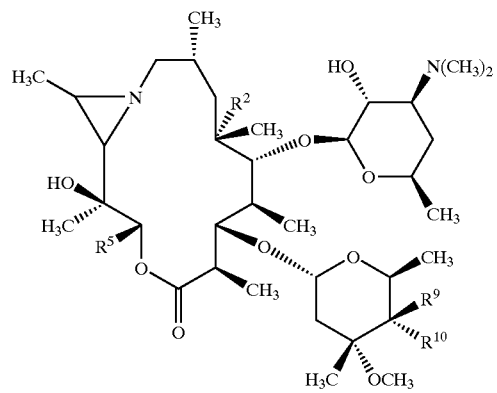

6 Claims, No Drawings

METHODS OF MAKING MACROLIDES

CROSS REFERENCE TO RELATED APPLICATIONS

This application is a divisional of and claims priority of U.S. non-provisional application Ser. No. 09/715,394, filed Nov. 17, 2000, now U.S. Pat, No, 6,518,251, issued Feb. 11, 2003 which claims priority of U.S. Provisional application No. 60/166,269, filed Nov. 18, 1999.

FIELD OF THE INVENTION

The invention is directed to novel macrolide derivatives, pharmaceutical compositions comprising them, and methods of using them in the treatment or prevention of, for example, bacterial or protozoa infections in mammals, fish, or birds.

BACKGROUND OF THE INVENTION

Macrolide antibiotics that can be used in the treatment or prevention of bacterial or protozoa infections in mammals, fish, or birds include various derivatives of erythromycin A, such as azithromycin, which is commercially available and is referred to in U.S. Pat. Nos. 4,474,768 and 4,517,359, both of which are incorporated herein by reference. Examples of additional macrolides are disclosed in: U.S. patent application Ser. No. 09/424,104, filed May 29, 1998 (Brian S. Bronk, Michael A. Letavic, Takushi Kaneko, Bingwei V. Yang, E. A. Glazer, and Hengmiao Cheng); WO 98/01571 (Peter Francis Leadlay, James Staunton, Jesus Cortes and Michael Stephen Pacey); WO 98/01546 (Peter Francis Leadlay, James Staunton, and Jesus Cortes); U.S. patent application Ser. No. 09/554,988, filed Dec. 21, 1998 (John P. Dirlam); U.S. Pat. No. 6,043,227, issued Mar. 28, 2000; and WO 98/09978, all of which are incorporated herein by reference.

SUMMARY OF THE INVENTION

This invention is directed to novel compounds of Formula 1:

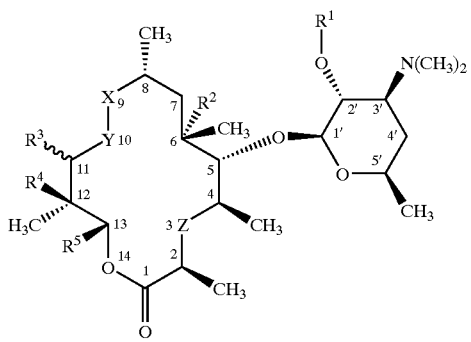

and to pharmaceutically acceptable salts, solvates, and prodrugs thereof, wherein:

X is —$CH_2NR^7$— or —$NR^7CHR^6$—, wherein the first dash of each of the foregoing X groups is attached to Y and the last dash of each of the foregoing X groups is attached to the C-8 carbon;

Y is —$CH(CH_3)$—;

or X, Y, and $R^3$ can be taken together to form the moiety of Formula a

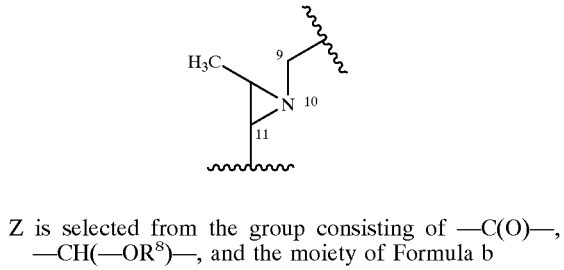

Z is selected from the group consisting of —C(O)—, —CH(—$OR^8$)—, and the moiety of Formula b

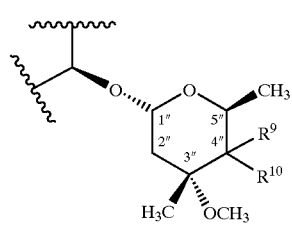

$R^1$ is H or a hydroxy protecting group;

$R^2$ is —$OR^{13}$, or $R^2$ and $R^3$ are taken together to form the moiety of Formula c

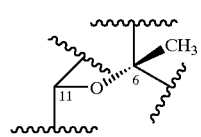

or if X is —$NR^7CHR^6$—, $R^2$ and $R^6$ can be taken together to form the moiety of Formula d

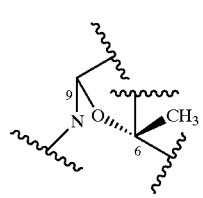

$R^3$ is —$OC(O)R^{14}$, or $R^3$, X, and Y are taken together to form the moiety of Formula a, or $R^3$ and $R^2$ are taken together to form the moiety of Formula c;

$R^4$ is —$OR^{15}$;

$R^5$ is an alpha-branched $C_2$–$C_8$ alkyl, $C_2$–$C_8$ alkenyl, $C_2$–$C_8$ alkynyl, $C_2$–$C_8$ alkoxyalkyl, or $C_2$–$C_8$ alkylthioalkyl group optionally substituted with at least one hydroxyl group; an alpha-branched $C_2$–$C_5$ alkyl group attached to a $C_5$–$C_8$ cycloalkyl group; a $C_3$–$C_8$ cycloalkyl or cycloalkenyl group optionally substituted with at least one moiety selected from the group consisting of methyl, hydroxyl, halo, and $C_1$–$C_4$ alkyl groups; or a 3–6 membered saturated, or fully or partially unsaturated, heterocycle comprising at least one atom of oxygen or sulphur and optionally substituted with one or more $C_1$–$C_4$ alkyl groups or halogen atoms;

$R^6$ is H, or if X is —$NR^7CHR^6$—, $R^6$ and $R^2$ can be taken together to form the moiety of Formula d;

$R^7$ is selected from the group consisting of H, $C_1$–$C_{10}$ alkyl, $C_2$–$C_{10}$ alkenyl, $C_2$–$C_{10}$ alkynyl, —$(CH_2)_m$ ($C_6$–$C_{10}$ aryl), and —$(CH_2)_m$(5–10 membered heteroaryl), wherein the alkyl, alkenyl, aryl, heteroaryl, and alkynyl moieties of the foregoing $R^7$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

$R_8$ is selected from the group consisting of H, $C_1$–$C_{10}$ alkyl, $C_2$–$C_{10}$ alkenyl, $C_2$–$C_{10}$ alkynyl, —C(O)$R^{17}$, —C(O)N$R^{17}R^{18}$, —$(CH_2)_m$($C_6$–$C_{10}$ aryl), and —$(CH_2)_m$(5–10 membered heteroaryl), wherein the alkyl, alkenyl, alkynyl, aryl, and heteroaryl moieties of the foregoing $R^8$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

$R^9$ is hydroxy;

$R^{10}$ is selected from the group consisting of H, $C_1$–$C_{10}$ alkyl, $C_2$–$C_{10}$ alkenyl, $C_2$–$C_{10}$ alkynyl, cyano, —$CH_2$S(O)$_nR^{11}$, —$CH_2$O$R^{11}$, —$CH_2$N$R^{11}R^{12}$, —$(CH_2)_m$($C_6$–$C_8$ aryl), and —$(CH_2)_m$(5–10 membered heteroaryl), wherein the alkyl, alkenyl, alkynyl, aryl, and heteroaryl moieties of the foregoing $R^{10}$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^1$ and $R^{12}$ is independently selected from the group consisting of H, $C_1$–$C_6$ alkyl, $C_2$–$C_6$ alkenyl, $(CH_2)_m$($C_6$–$C_{10}$ aryl), $(CH_2)_m$(5–10 membered heteroaryl), and $C_2$–$C_{10}$ alkynyl, wherein the alkyl, alkenyl, aryl, heteroaryl, and alkynyl moieties of the foregoing $R^{11}$ and $R^{12}$ groups are optionally substituted with 1 to 3 substituents independently selected from the group consisting of halo, cyano, nitro, trifluoromethyl, $C_1$–$C_6$ alkyl, and $C_1$–$C_6$ alkoxy;

$R^{13}$ is selected from the group consisting of H, $C_1$–$C_{10}$ alkyl, $C_2$–$C_{10}$ alkenyl, $C_2$–$C_{10}$ alkynyl, —$R^{16}$($C_6$–$C_{10}$ aryl), and —$R^{16}$(5–10 membered heteroaryl), wherein the alkyl, alkenyl, alkynyl, aryl, and heteroaryl moieties of the foregoing $R^{13}$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

$R^{14}$ is selected from the group consisting of $C_1$–$C_{10}$alkyl, $C_2$–$C_{10}$ alkenyl, $C_2$–$C_{10}$ alkynyl, —$(CH_2)_m$($C_6$–$C_{10}$ aryl), and —$(CH_2)_m$(5–10 membered heteroaryl), wherein the alkyl, alkenyl, aryl, heteroaryl, and alkynyl moieties of the foregoing $R^{14}$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^{15}$ is independently selected from the group consisting of H, $C_1$–$C_{10}$ alkyl, $C_2$–$C_{10}$-alkenyl, $C_2$–$C_{10}$ alkynyl, —$(CH_2)_m$($C_6$–$C_{10}$ aryl), and —$(CH_2)_m$(5–10 membered heteroaryl), wherein the alkyl, alkenyl, alkynyl, aryl, and heteroaryl moieties of the foregoing $R^{15}$ groups are optionally substituted with 1 to 3 substituents independently selected from the group consisting of halo, cyano, nitro, trifluoromethyl, azido, —C(O)$R^{11}$—OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl;

$R^{16}$ is selected from the group consisting of $C_1$–$C_6$ alkyl, $C_3$–$C_6$ alkenyl, and $C_3$–$C_6$ alkynyl, wherein the alkyl, alkenyl, and alkynyl moieties of the foregoing $R^{16}$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R_{11}R_{12}$, —N$R^{11}R^{12}$, hydroxy, $C_1$–$C_6$ alkyl, $C_1$–$C_6$ alkoxy, $C_6$–$C_{10}$ aryl, and 5–10 membered heteroaryl, and wherein at least one carbon atom of each of the foregoing $R^{16}$ groups can optionally be replaced with 1 to 3 atoms or moieties independently selected from group consisting of O, N($R^{15}$), and S;

each of $R^{17}$ and $R^{18}$ is independently selected from the group consisting of H, $C_1$–$C_{10}$ alkyl, $C_2$–$C_{10}$ alkenyl, $C_2$–$C_{10}$ alkynyl, —$(CH_2)_m$($C_6$–$C_{10}$ aryl), and —$(CH_2)_m$(5–10 membered heteroaryl), wherein the alkyl, alkenyl, alkynyl, aryl, and heteroaryl moieties of the foregoing $R^{17}$ and $R^{18}$ groups are optionally substituted with 1 to 3 substituents independently selected from the group consisting of halo, cyano, nitro, trifluoromethyl, azido, —C(O)$R^{11}$, —OC(O)$R^{11}$, —N$R^{11}$C(O)$R^{12}$, —C(O)N$R^{11}R^{12}$, —N$R^{11}R^{12}$, hydroxy, $C_1$–$C_6$ alkyl, $C_1$–$C_6$ alkoxy, $c_6$–$C_{10}$ aryl, and 5–10 membered heteroaryl;

each n independently represents an integer of from 0 to 2; and each m independently represents an integer of from 0 to 4.

In a preferred compound of Formula 1, X is —$CH_2$N$R^7$— or —N$R^7$CH$R^6$—, Z is a moiety of Formula b, $R^2$ is OH, $R^3$ is —OC(O)$R^{14}$, $R^4$ is OH, and $R^6$ is H.

In another preferred compound of Formula 1, X is —N$R^7$CH$R^6$—, Z is a moiety of Formula b, $R^2$ and $R^6$ are taken together to form a moiety of Formula d, $R^3$ is —OC(O)$R^{14}$, $R^4$ is OH, and $R^7$ is $CH_3$.

In another preferred compound of Formula 1, X, Y, and $R^3$ are taken together to form a moiety of Formula a, Z is a moiety of Formula b, $R^2$ is OH, and $R^4$ is OH.

In another preferred compound of Formula 1, X is —$CH_2$N$R^7$— or —N$R^7$CH$R^6$—, Z is a moiety of Formula b, $R^2$ and $R^3$ are taken together to form a moiety of Formula c, and $R^4$ is OH.

In another preferred compound of Formula 1, X, Y, and $R^3$ are taken together to form a moiety of Formula a, Z is —CH(O$R^8$)—, $R^2$ is —O$R^{13}$, and $R^4$ is O$R^{15}$.

In another preferred compound of Formula 1, X, Y, and $R^3$ are taken together to form a moiety of Formula a, Z is —C(O)—, $R^2$ is —O$R^{13}$, and $R^4$ is O$R^{15}$. In a more preferred compound of Formula 1, $R^1$ is H; $R^5$ is ethyl; $R^{15}$ is H or methyl, and $R^{13}$ is a moiety of Formula e–g e

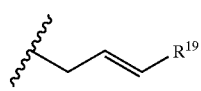

-continued

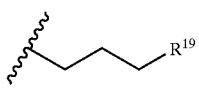
f

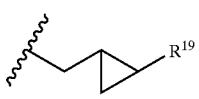
g wherein $R^{19}$ is $C_6$–$C_{10}$ aryl or 5–10 membered heteroaryl, wherein the aryl and heteroaryl moieties of the foregoing $R^{19}$ groups are optionally substituted with 1 to 3 substituents selected from the group consisting of halo, cyano, nitro, trifluoromethyl, azido, —C(O)$R^{11}$, —OC(O)$R^{12}$, —$NR^{11}$C(O)$R^{12}$, —C(O)$NR^{11}R^{12}$, —$NR^{11}R^{12}$, hydroxy, $C_1$–$C_6$ alkyl, $C_1$–$C_6$ alkoxy, $C_6$–$C_{10}$ aryl, and 5–10 membered heteroaryl. In an even more preferred compound of Formula 1, $R^{19}$ is selected from the group consisting of phenyl, 2-quinolyl, 3-quinolyl, 4-quinolyl, 5-quinolyl, 6-quinolyl, 7-quinolyl, 8-quinolyl, 2-pyridyl, 3-pyridyl, and 4-pyridyl.

In another preferred compound of Formula 1, $R^5$ is selected from the group consisting of ethyl, isopropyl, cyclopropyl, sec-butyl, cyclobutyl, cyclopentyl, methylthioethyl, and furyl.

The invention further encompasses a method of preparing a compound of Formula 2

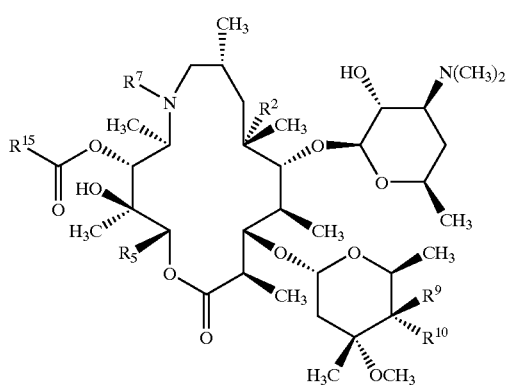
2 wherein $R^2$, $R^5$, $R^9$, $R^{10}$, and $R^{15}$ are defined herein, which comprises contacting a compound of Formula f

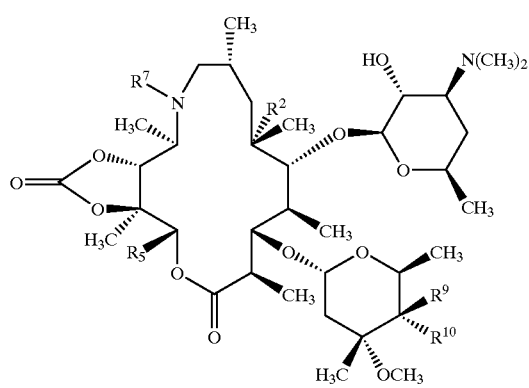
f with a Grignard reagent for a time and at a temperature sufficient to form a compound of Formula 2.

The invention further encompasses a method of preparing a compound of Formula 4

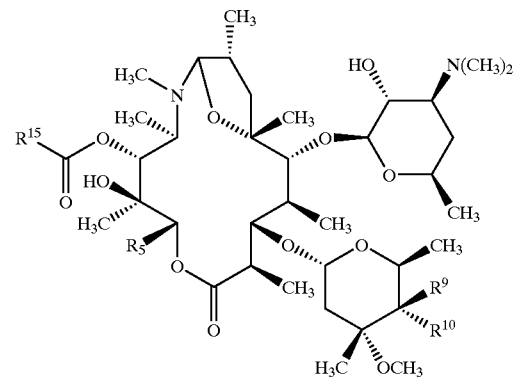
4 wherein $R^5$, $R^9$, $R^{10}$, and $R^{15}$ are defined herein, which comprises contacting a compound of Formula h

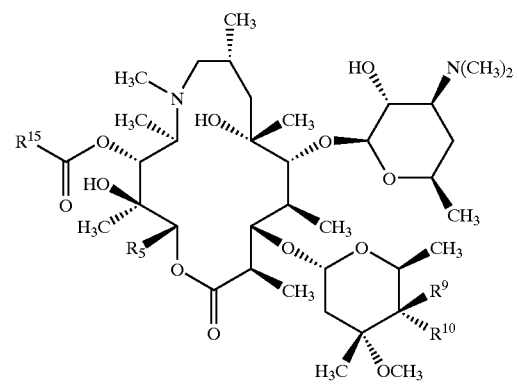
h with an amine oxidizing reagent for a time and at a temperature sufficient to form a compound of Formula 4. In a preferred embodiment of the invention, the amine oxidizing reagent is selected from the group consisting of N-bromosuccinimide, N-chlorosuccinimide, iodine, and bromine.

The invention further encompasses a method of preparing a compound of Formula 5

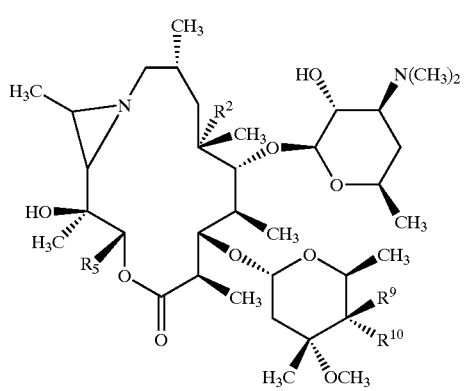
5 wherein $R^2$, $R^5$, $R^9$, and $R^{10}$ are defined herein, which comprises contacting a compound of Formula i

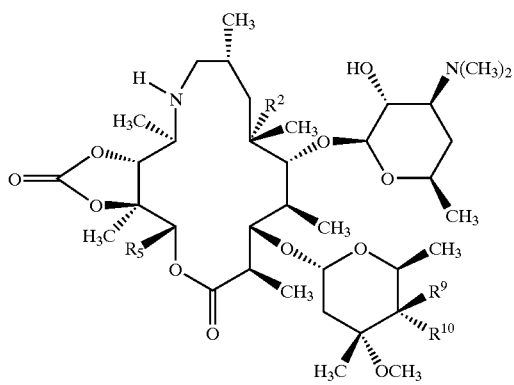

with a Grignard reagent or a base for a time and at a temperature sufficient to form a compound of Formula 5. In a preferred method, the Grignard reagent is benzyl magnesium chloride. In another preferred method, the base is isopropylcyclohexylamino magnesium chloride.

The invention further encompasses a method of forming a compound of Formula 7

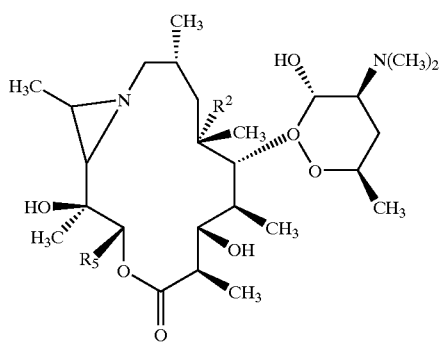

wherein $R^2$ and $R^5$ are defined herein, which comprises contacting a compound of Formula 5

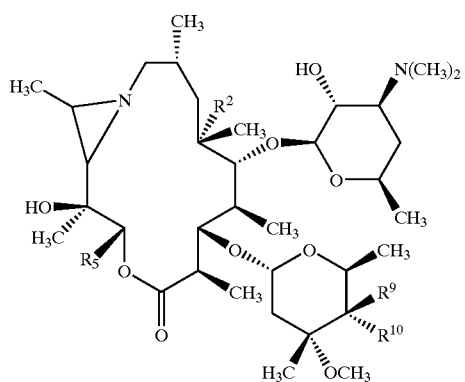

wherein $R^9$ and $R^{10}$ are defined herein, with acidic conditions for a time and at a temperature sufficient to form a compound of Formula 7.

The invention further encompasses pharmaceutical compositions comprising a compound of Formula 1 or a pharmaceutically acceptable salt, solvate, or prodrug thereof and a pharmaceutically acceptable carrier.

The invention further encompasses a method of treating a bacterial or protozoal infection in a mammal, fish, or bird which comprises administering to a mammal, fish or bird in need of such treatment a therapeutically effective amount of a compound of Formula 1 or a pharmaceutically acceptable salt, solvate, or prodrug thereof.

DEFINITIONS

As used herein and unless otherwise indicated, the term "infection(s)" includes bacterial infection(s) and protozoa infection(s) that occur in mammals, fish or birds as well as disorders related to bacterial infections and protozoa infections that may be treated or prevented by administering antibiotics such as the compounds of the invention. Such bacterial infections and protozoa infections and disorders related to such infections include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or Peptostreptococcus spp.; pharyngitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chiamydia pneumoniae*; uncomplicated skin and soft tissue infections, abscesses and osteomyelitis, and puerperal fever related to infection by *Staphylococcus aureus*, coagulase-positive staphylococci (e.g., *S. epidermidis* and *S. hemolyticus*), *Streptococcus pyogenes , Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylon*; systemic febrile syndromes related to infection by *Borrelia recurrentis*; Lyme disease related to infection by Borrelia burgdorferi; conjunctivitis, keratitis, and dacrocystitis related to infection by *Chlamydia trachomatis, Neisseria gonorrhoeae, S. aureus, S. pneumoniae, S. pyogenes, H. influenzae*, or Listeria spp.; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory disease related to infection by *P. haem., P. multocida, Mycoplasma bovis*, or Bordetella spp.; cow enteric disease related to infection by *E. coli* or protozoa (e.g., coccidia and cryptosporidia); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia*

*intracellularis*, Salmonella, or *Serpulina hyodyisinteriae*; cow footrot related to infection by Fusobacterium spp.; cow metritis related to infection by *E. coli*; cow hairy warts related to infection by Fusobacterium necrophorum or Bacteroides nodosus; cow pink-eye related to infection by *Moraxella bovis*; cow premature abortion related to infection by protozoa (e.g., neosporium); urinary tract infection in dogs and cats related to infection by *E. coli*; skin and soft tissue infections in dogs and cats related to infection by *Staph. epidermidis, Staph. intermedius, coagulase* neg. Staph. or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoa infections and disorders related to such infections that may be treated or prevented in accord with the method of the present invention are referred to in J. P. Sanford et al., "The Sanford Guide To Antimicrobial Therapy," 26$^{th}$ Edition, (Antimicrobial Therapy, Inc., 1996).

As used herein and unless otherwise indicated, the term "treatment" includes treatment or prevention.

As used herein and unless otherwise indicated, the term "halo" means fluoro, chloro, bromo or iodo. Preferred halo groups are fluoro, chloro and bromo.

As used herein and unless otherwise indicated, the term "alkyl" includes saturated monovalent hydrocarbon radicals having straight, cyclic or branched moieties, or a combination of the foregoing moieties. An alkyl group can include one or two double or triple bonds. It is understood that cyclic alkyl groups comprise at least three carbon atoms.

As used herein and unless otherwise indicated, the term "alkanoyl" includes —C(O)-alkyl groups wherein "alkyl" is defined herein.

As used herein and unless otherwise indicated, the term "aralkyl" includes an aryl substituted with an alkyl group or an alkyl substituted with an aryl group.

As used herein and unless otherwise indicated, the term "aryl" includes an organic radical derived from an aromatic hydrocarbon by removal of one hydrogen, such as phenyl or naphthyl.

As used herein and unless otherwise indicated, "Ac" indicates an acetyl group.

As used herein and unless otherwise indicated, "Me" indicates a methyl group.

As used herein and unless otherwise indicated, "Et" indicates an ethyl group.

As used herein and unless otherwise indicated, the term "heteroaryl" means an aryl group wherein at least one carbon atom has been replaced with an atom selected from the group consisting of O, S, and N.

As used herein and unless otherwise indicated, the terms "heterocyclic group" and "heterocycle" include aromatic and non-aromatic heterocyclic groups containing one or more heteroatoms each selected from O, S and N. Non-aromatic heterocyclic groups include groups having only 3 atoms in their ring system, but aromatic heterocyclic groups (i.e., heteroaryl groups) must have at least 5 atoms in their ring system. Heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl, and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such attachment is possible. For instance, a group derived from pyrrole can be pyrrol-1-yl (N-attached) or pyrrol-3-yl (C-attached).

As used herein and unless otherwise indicated, the phrase "pharmaceutically acceptable salt(s)" includes salts of acidic or basic groups which may be present in the compounds of the present invention. The compounds of the present invention that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, such as, but not limited to, the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate [i.e., 1,1'-methylene-bis-(2-hydroxy-3-naphthoate)] salts. Compounds of the invention that include a basic moiety, such as an amino group, can form pharmaceutically acceptable salts with various amino acids in addition to the acids mentioned above.

Those compounds of the present invention that are acidic in nature are capable of forming base salts with various pharmacologically acceptable cations. Examples of such salts include the alkali metal or alkaline earth metal salts, and calcium, magnesium, sodium and potassium salts in particular.

In the chemical structures depicted herein, a wavy line indicates that the stereochemistry at the chiral center to which the wavy line is connected is either an R or S configuration where the wavy line is connected to a carbon atom.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. Compounds of Formula 1 can also exist as tautomers. This invention relates to the use of all such tautomers and mixtures thereof.

This invention further encompasses isotopically-labeled compounds of Formula 1 which are identical to those of Formula 1 but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F, and $^{36}$Cl, respectively. Isotopically labeled compounds of Formula 1, and pharmaceutically acceptable salts, solvates, and prodrugs thereof are encompassed by this invention. Certain isotopically-labeled compounds of the present invention, for example those into which radioactive isotopes such as $^3$H and $^{14}$C are incorporated, are useful in drug and/or substrate tissue distribution assays. Tritiated (i.e., 3H) and carbon-14 (i.e., $^{14}$C) isotopes are particularly preferred for their ease of preparation and detectability. Further, substitution with heavier isotopes such as deuterium (i.e., $^2$H) can afford certain therapeutic advantages resulting from greater metabolic stability, for example increased in vivo half-life or reduced dosage requirements and, hence, may be preferred in some circumstances. Isotopically labeled compounds of the invention and prodrugs thereof can generally be prepared by carrying out the procedures disclosed herein by substituting a readily available isotopically labeled reagent for a non-isotopically labeled reagent.

This invention also encompasses pharmaceutical compositions containing prodrugs of compounds of Formula 1 and methods of treating bacterial or protozoal infections which comprise the administration of prodrugs of compounds of Formula 1. Compounds of the invention having free amino, amido, hydroxy, or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of Formula 1. The amino acid residues include, but are not limited to, the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed by the invention. For instance, free carboxyl groups can be derivatized as amides or alkyl esters. The amide and ester moieties can incorporate groups including, but not limited to, ether, amine, and carboxylic acid functionalities. Free hydroxy groups can be derivatized using groups including, but not limited to, hemisuccinates, phosphate esters, dimethylaminoacetates, and phosphoryloxymethyl-oxycarbonyls, as outlined in D. Fleisher, R. Bong, B. H. Stewart, *Advanced Drug Delivery Reviews* 19:115 (1996). Carbamate prodrugs of hydroxy and amino groups are also encompassed by the invention, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed by the invention. Prodrugs of this type are described in R. P. Robinson et al., *J. Medicinal Chemistry* 39:10 (1996).

DETAILED DESCRIPTION OF THE INVENTION

This invention is directed to novel macrolide compounds, to methods of making them, and to pharmaceutical compositions comprising them. The invention is further directed to methods of treating or preventing bacterial and protozoal infections in mammals (e.g., humans), fish, and birds, as well as to methods of treating or preventing other diseases and conditions such as, but not limited to, cancer, atherosclerosis, and gastric motility disorders.

Specific compounds of the invention are of Formula 2, and are listed in Table 1:

TABLE 1

| Compound | $R^2$ | $R^5$ | $R^7$ | $R^9$ | $R^{10}$ | $R^{15}$ | MS | Yield % |
|---|---|---|---|---|---|---|---|---|
| 2(a) | OH | Ethyl | Me | H | OH | Phenyl | 853.3 | 14 |
| 2(b) | OH | Ethyl | H | H | OH | Allyl | 803.3 | 30 |
| 2(c) | OH | Ethyl | Me | H | OH | Allyl | 817.3 | 27 |
| 2(d) | OH | Ethyl | Propyl | H | OH | p-Chlorophenyl | 915.2 | 14 |
| 2(e) | OH | Ethyl | H | H | OH | Vinyl | 789 | 27 |
| 2(f) | OH | Ethyl | Propyl | H | OH | Allyl | 845.3 | 16 |
| 2(g) | OH | Ethyl | H | H | OH | p-Fluorophenyl | 857.3 | 19 |
| 2(h) | OH | Ethyl | Me | H | OH | p-Fluorophenyl | 871.2 | 2.4 |
| 2(i) | OH | Ethyl | Propyl | H | OH | p-Fluorophenyl | 899.4 | 24 |
| 2(j) | OH | Ethyl | H | H | OH | p-Chlorophenyl | 873.2 | 13 |
| 2(k) | OH | Ethyl | Me | H | OH | p-Chlorophenyl | 877.0 | 5.4 |
| 2(l) | OH | Ethyl | Propyl | H | OH | Vinyl | 831.3 | 10 |
| 2(m) | OH | Ethyl | Me | H | OH | Vinyl | 803.3 | 46 |
| 2(n) | OH | Ethyl | Me | H | OH | Me | 791.5 | 40 |

The mass spectra (MS) and yield information provided in Table 1 are with regard to the preparation of compounds 2(a)–2(n) as described below in the Examples. Compounds of Formula 2 can be prepared according to the method shown in Scheme 1:

Scheme 1

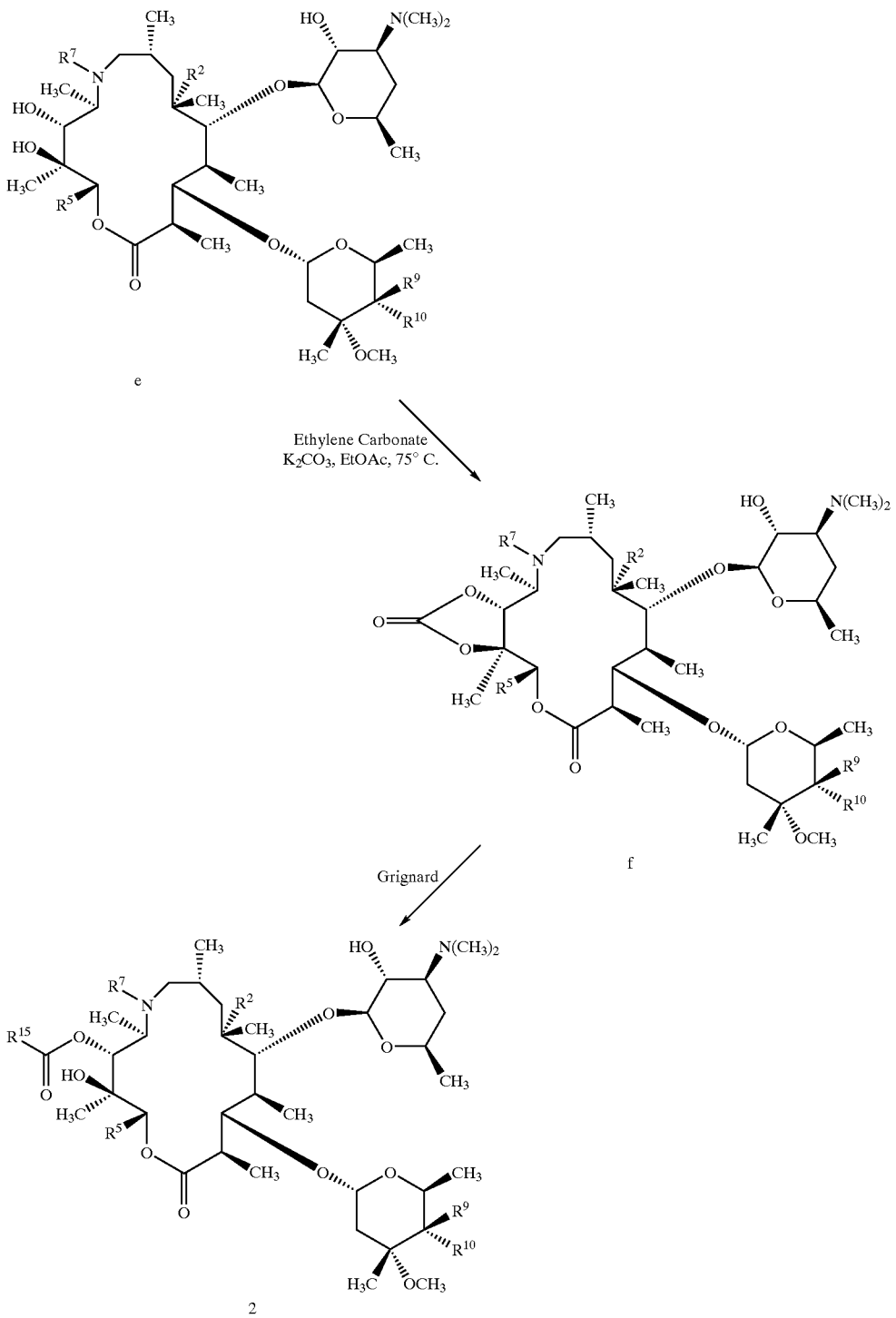

According to Scheme 1, compounds of Formula 2 can be prepared from compounds of Formula e, the synthesis of which is disclosed by U.S. Pat. Nos. 4,474,768 and 4,517,359, both of which are incorporated herein by reference. According to this method, a carbonate compound of Formula f is prepared from compound e using synthetic conditions known to those skilled in the art. Preferred conditions comprise the use of ethylene carbonate and a base such as potassium carbonate in a solvent such as ethyl acetate. The carbonate f can then be reacted with a Grignard reagent to provide compound 2.

Other compounds of the invention are those of Formula 3, specific examples of which are listed in Table 2:

TABLE 2

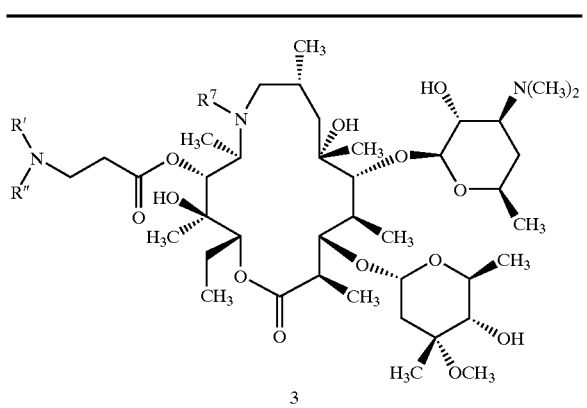

3

| Compound | R⁷ | R' | R" | MS | Yield |
|---|---|---|---|---|---|
| 3(a) | Me | H | 2-Thiophenylethyl | 930.6 | 75 |
| 3(b) | Me | Me | Ethyl | 862.3 | 79 |
| 3(c) | Me | H | Cyclobutyl | 874.4 | 84 |
| 3(d) | Me | H | 3-Pyridylethyl | 925.6 | 43 |
| 3(e) | Me | H | 3-Pyridylmethyl | 911.6 | 36 |
| 3(f) | Me | H | 3-Chlorobenzyl | 944.6 | 93 |
| 3(g) | Me | H | 2-furylmethyl | 900.6 | 60 |
| 3(h) | Me | H | 4-Pyridylethyl | 925.4 | 48 |
| 3(i) | Me | H | 2-Pyridylethyl | 925.4 | 55 |
| 3(j) | Me | H | 2-Pyridylmethyl | 911.4 | 56 |
| 3(k) | Me | H | 4-Pyridylmethyl | 911.4 | 53 |
| 3(l) | Me | H | t-Butyl | 876.5 | 85 |
| 3(m) | Me | H | 3-Indole-ethyl | 963.3 | 16 |

As above, the MS and yield information provided in Table 2 are with regard to the preparation of compounds 3(a)–3(m) as described below in the Examples. Compounds of Formula 3 can be prepared according to the method shown in Scheme 2:

Scheme 2

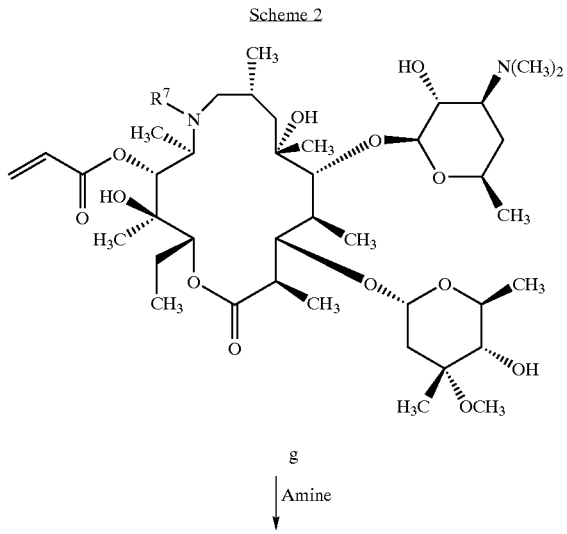

g

↓ Amine

-continued

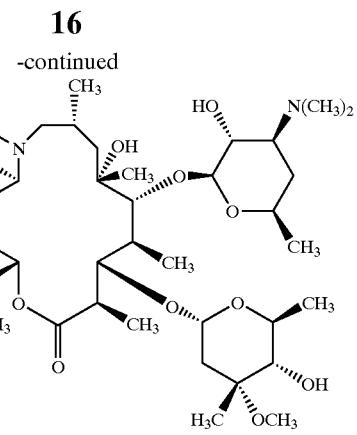

3

According to Scheme 2, compounds of Formula 3 can be readily prepared from compounds of Formula g, which can be prepared according to Scheme 1. In particular, compounds of Formula 3 can be prepared by dissolving compounds of Formula g in a liquid amine and subsequently stirring the resulting mixture for a sufficient time and at a sufficient temperature (e.g., about 2 days at room temperature). Alternatively, compounds of Formula g and a liquid or solid amine can be dissolved in a solvent, which can then be stirred for a sufficient time and at a sufficient temperature to yield compounds of Formula 3.

Still other compounds of the invention are those of Formula 4, specific examples of which are listed in Table 3:

TABLE 3

4

| Compound | R⁵ | R⁹ | R¹⁰ | R¹⁵ | MS | Yield % |
|---|---|---|---|---|---|---|
| 4(a) | Ethyl | H | OH | Me | 789.4 | 52 |
| 4(b) | Ethyl | H | OH | Vinyl | 801.5 | 33 |

Wherein the MS and yield information provided in Table 3 are with regard to the preparation of compounds 4(a)–4(b) as described below in the Examples. Compounds of Formula 4 can be prepared according to the method shown in Scheme 3:

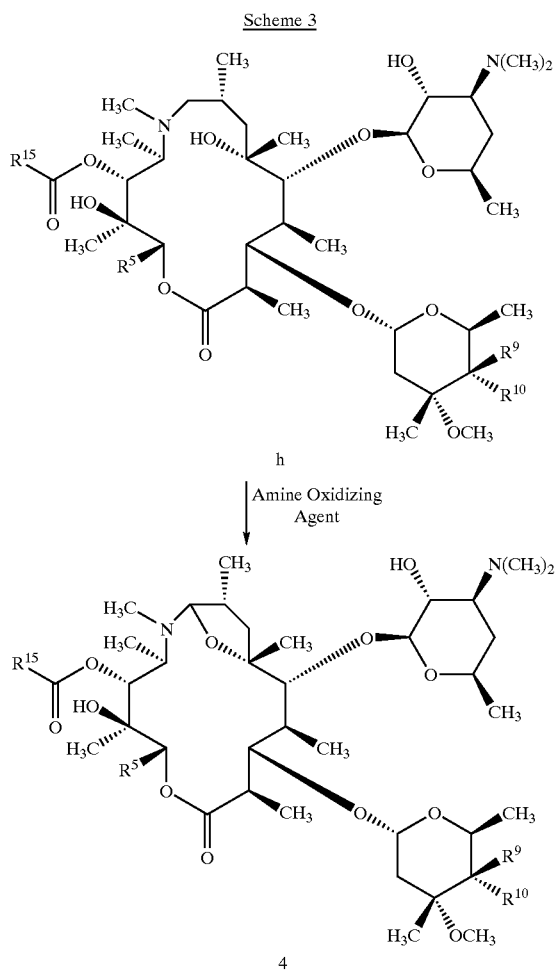

Scheme 3

According to Scheme 3, compounds of Formula 4 can be readily prepared from compounds of Formula h, which in turn can be prepared according to the method of Scheme 1. In particular, compounds of Formula 4 can be prepared by reacting compounds of Formula h with an amine oxidizing reagent in a suitable solvent such as, but not limited to, ethyl acetate and tetrahydrofuran (THF). Suitable amine oxidizing agents include, but are not limited to, N-bromosuccinimide (NBS), N-chlorosuccinimide (NCS), iodine, and bromine.

Other examples of compounds of the invention and preferred methods of their synthesis are provided in the Examples below.

Compounds of the present invention can have asymmetric carbon atoms, and diastereomeric mixtures of them can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

Compounds of the invention (i.e., compounds of Formula 1) that are basic in nature are capable of forming a wide variety of different salts with various inorganic and organic acids. Although such salts must be pharmaceutically acceptable for administration to animals, it is often desirable in practice to initially isolate the compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Compounds of the invention that are acidic in nature are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of the invention. Non-toxic base salts include those derived from such pharmacologically acceptable cations such as, but not limited to, sodium, potassium calcium, and magnesium. These salts can be prepared by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown below in Table 4. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase that generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains can be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", *Antimicrobial Agents and Chemotherapy*, 40(11):2562–2566 (1996). The antibacterial assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare strains. acr AB or acr AB-like indicates that an intrinsic multidrug efflux pump exists in the strain. Compounds are initially dissolved in dimethylsulfoxide (DMSO) as 40 mg/mL stock solutions.

TABLE 4

| Strain Designation | Macrolide Resistance Mechanism(s) |
| --- | --- |
| *Staphylococcus aureus* 1116 | Susceptible parent |
| *Staphylococcus aureus* 1117 | ErmB |
| *Staphylococcus aureus* 0052 | Susceptible parent |
| *Staphylococcus aureus* 1120 | ErmC |
| *Staphylococcus aureus* 1032 | MsrA, mph, esterase |
| *Staphylococcus hemolyticus* 1006 | MsrA, mph |
| *Streptococcus pyogenes* 0203 | Susceptible parent |
| *Streptococcus pyogenes* 1079 | ErmB |
| *Streptococcus pyogenes* 1062 | Susceptible parent |
| *Streptococcus pyogenes* 1061 | ErmB |
| *Streptococcus pyogenes* 1064 | MefA |
| *Streptococcus agalactiae* 1024 | Susceptible parent |
| *Streptococcus agalactiae* 1023 | ErmB |
| *Streptococcus pneumoniae* 1016 | Susceptible |
| *Streptococcus pneumoniae* 1046 | ErmB |
| *Streptococcus pneumoniae* 1095 | ErmB |
| *Streptococcus pneumoniae* 1175 | MefE |
| *Haemophilus influenzae* 0085 | Susceptible; acr AB-like |
| *Haemophilus influenzae* 0131 | Susceptible; acr AB-like |
| *Moraxella catarrhalis* 0040 | Susceptible |
| *Moraxella catarrhalis* 1055 | Erythromycin intermediate resistance |
| *Escherichia coli* 0266 | Susceptible; acr AB |
| *Haemophilus influenzae* 1100 | Susceptible; acr AB-like |

Assay II, as described below, is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 mL of brain heart infusion (BHI) broth. The test compounds are prepared by solubilizing 1 mg of the compound in 125 mL of dimethylsulfoxide (DMSO). Dilutions of the test compound are prepared using uninoculated BHI broth. The concentrations of the test compound used range from 200 mg/mL to 0.098 mg/mL by two-fold serial dilutions. The *P. multocida* inoculated BHI is diluted with uninoculated BHI broth to make a $10^4$ cell suspension per 200 ml. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 mL of the fully grown *P. haemolytica* preculture is inoculated into 3 mL of fresh BHI broth and is incubated at 37° C. with shaking (200 rpm). The appropriate amounts of the test compounds are dissolved in ethanol and a series of two-fold serial dilutions are prepared. Two mL of the respective serial dilution is mixed with 18 mL of molten BHI agar and solidified. When the inoculated *P. haemolytica* culture reaches 0.5 McFarland standard density, about 5 mL of the *P. haemolytica* culture is inoculated onto BHI agar plates containing the various concentrations of the test compound using a Steers Replicator and incubated for 18 hours at 37° C. Initial concentrations of the test compound range from about 100 to about 200 mg/mL. The MIC is equal to the concentration of the test compound exhibiting 100% inhibition of growth of *P. haemolytica* as determined by comparison with an uninoculated control.

The in vivo activity of the compounds of the invention can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 mL of a $3 \times 10^3$ CFU/mL bacterial suspension (*P. multocida* strain 59A006) intraperitoneally. Each experiment has at least 3 non-medicated control groups including one infected with 0.1× challenge dose and two infected with 1×challenge dose; a 10×challenge data group may also be used. Generally, all mice in a given study can be challenged within about 30 to about 90 minutes, especially if a repeating syringe (such as a Cornwalla syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 mL is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infection which would be lethal in the absence of drug treatment.

The compounds of the invention and their pharmaceutically acceptable salts, solvates and prodrugs (herein also referred to as "active compounds of this invention") can be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining the active compounds of this invention can then be readily administered in a variety of dosage forms such as, but not limited to, tablets, powders, lozenges, syrups, and injectable solutions. These pharmaceutical compositions can, if desired, contain additional ingredients such as, but not limited to, flavorings, binders, and excipients. Thus, for purposes of oral administration, tablets containing various excipients such as sodium citrate, calcium carbonate, and calcium phosphate may be employed along with various disintegrants such as starch, methylcellulose, alginic acid, and certain complex silicates, together with binding agents such as polyvinylpyrrolidone, sucrose, gelatin, and acacia. Additionally, lubricating agents such as magnesium stearate, sodium lauryl sulfate and talc are often useful for tableting purposes. Solid compositions of a similar type can also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein can be combined with various sweetening or flavoring agents, coloring matter or dyes and, if desired, emulsifying or suspending agents, together with diluents such as water, ethanol, propylene glycol, glycerin, and combinations thereof.

For parenteral administration, solutions containing an active compound of this invention or a pharmaceutically acceptable salt thereof in sesame or peanut oil, aqueous propylene glycol, or in sterile aqueous solution can be employed. Such aqueous solutions should be suitably buffered if necessary and the liquid diluent first rendered isotonic with sufficient saline or glucose. These particular aqueous solutions are especially suitable for intravenous, intramuscular, subcutaneous, and intraperitoneal administration. The sterile aqueous media employed are all readily available by standard techniques known to those skilled in the art.

To implement the methods of this invention, an effective dose of an active compound of this invention is administered to a susceptible or infected animal (including mammals, fish and birds) by parenteral (i.v., i.m. or s.c.), oral, or rectal routes, or locally as a topical application to the skin and/or mucous membranes. The route of administration will depend on the mammal, fish or bird that is being treated. The effective dose will vary with the severity of the disease, and the age, weight and condition of the animal. However, the daily dose will usually range from about 0.25 to about 150 mg/kg body weight of the patient to be treated, preferably from about 0.25 to about 25 mg/kg.

The Examples provided below illustrate specific embodiments of the invention, but the invention is not limited in scope to the Examples specifically exemplified.

EXAMPLES 1–12

Synthesis of Compounds 2(a)–2(I)

Compounds 2(a)–2(I), the structures of which are provided by Table 1, were prepared as shown in Scheme 1 from the azalide derivative e, the synthesis of which is disclosed by U.S. Pat. Nos. 4,474,768 and 4,517,359.

The derivative e (10 g) was dissolved in EtOAc (150 mL), followed by the addition of ethylene carbonate (10 eq) and $K_2CO_3$ (2 eq). The resulting solution was stirred at 75° C. for one to five days, and the reaction was followed by TLC. After the reaction was completed, the reaction mixture was cooled to room temperature, and diluted with EtOAc (250 mL) and water (100 mL). The organic layer was washed with water (4×100 mL), brine (2×100 mL), and dried ($Na_2SO_4$). The solvent was then removed in vacuo to give the crude product which was purified either by flash chromatography using 3% MeOH and 0.5% ammonia in $CH_2Cl_2$ or by recrystallization from $CH_3CN$ to give compound f (shown in Scheme 1) typically in a yield of greater than about 80%.

Azalide carbonate f (0.5 mmol–5 mmol) was dissolved in $CH_2Cl_2$ (10 mL–100 mL) and cooled to –78° C. The Grignard reagent (e.g., vinyl magnesium bromide) (6–10 equivalents) was then slowly added at this temperature, and the reaction was followed by TLC. If there was no reaction at this temperature, the reaction mixture was then warmed to higher temperature. After the reaction was complete, usually between 15 minutes to 4 hours, it was quenched with saturated $NH_4Cl$ solution (25 mL–250 mL). The aqueous layer was extracted with $CH_2Cl_2$ (100 mL–500 mL), and the organic layer was then washed with saturated $NaHCO_3$ solution (25 mL–100 mL), brine (25 mL–100 mL). The organic layer was dried with $Na_2SO_4$, and the solvent was removed in vacuo to give the crude product of Formula 2, which was purified by flash chromatography using 1–5% MeOH and 0.5% ammonia in $CH_2Cl_2$.

EXAMPLE 13

Synthesis of Compound 2(m)

Azalide carbonate f, shown in Scheme 1 and prepared according to Examples 1–12, wherein $R^7$ is methyl (3.00 g, 3.87 mmol) was dissolved in a mixture of ethylene glycol dimethylether (75 mL) and N,N,N',N'-tetramethylethylenediamine (30 mL). The reaction solution was cooled to –78° C., and 1 M vinyl magnesium bromide in THF (31 mL, 31 mmol) was then slowly added at this temperature. After the stirring was continued for 2 hours at –78° C., the reaction was quenched with saturated $NH_4Cl$ solution (100 mL). The aqueous layer was extracted with EtOAc (400 mL), and the organic layer was washed with saturated $NaHCO_3$ solution (50 mL), brine (50 mL). The organic layer was then dried with $Na_2SO_4$, and the solvent was removed in vacuo to give the crude product which was purified by flash chromatography using 5% MeOH and 0.5% ammonia in $CH_2Cl_2$ (1.43 g, 46%).

EXAMPLE 14

Synthesis of Compound 2(n)

Azalide carbonate f, shown in Scheme 1 and prepared according to Examples 1–12, wherein $R^7$ is methyl (3.00 g, 3.87 mmol) was dissolved in a mixture of ethylene glycol dimethylether (75 mL) and N,N,N',N'-tetramethylethylenediamine (30 mL). The reaction solution was cooled to –40° C., and 3 M methyl magnesium bromide in ether solution (12.9 mL, 38.7 mmol) was then slowly added at this temperature. After the stirring was continued for 2 hours at –40° C., the reaction was quenched with saturated $NH_4Cl$ solution (100 mL). The aqueous layer was extracted with EtOAc (400 mL), and the organic layer was washed with saturated $NaHCO_3$ solution (50 mL), brine (50 mL). The organic layer was then dried with $Na_2SO_4$, and the solvent was removed in vacuo to give the crude product which was purified by flash chromatography using 5% MeOH and 0.5% ammonia in $CH_2Cl_2$ (1.08 g, 40%).

EXAMPLES 15–26

Synthesis of Compounds 3(a)–3(I)

Compounds 3(a)–3(I), the structures of which are provided by Table 2, were prepared as shown in Scheme 2 from the azalide derivative g, which can be prepared according to Scheme 1 and Example 13.

Azalide derivative g ( 50–200 mg) was dissolved in 0.2–1.0 mL of the appropriate amine (e.g., t-butylamine) and the reaction mixture was stirred at room temperature for 2 days. The reaction mixture was then diluted with $CH_2Cl_2$ (200 mL), and washed with water (6 ×25 mL), and brine (25 mL). The organic layer was then dried with $Na_2SO_4$, and the solvent was removed in vacuo to give the crude product which was purified by flash chromatography using 3–5% of 2M ammonia in MeOH solution in $CH_2Cl_2$.

EXAMPLE 27

Synthesis of Compound 3(m)

Azalide derivative g, shown in Scheme 2, wherein $R^7$ is methyl (188 mg, 0.234 mmol) and tryptamine (129 mg, 0.802 mmol) were dissolved in THF (2 mL), and the reaction mixture was stirred at room temperature for 25 hours. The reaction mixture was then diluted with $CH_2Cl_2$ (200 mL), and washed with 0.1 M pH 7 sodium phosphate buffer (3×25 mL). The organic layer was then washed with brine (25 mL), and dried with $Na_2SO_4$. The solvent was evaporated in vacuo to give the crude product which was purified by flash chromatography using 5% 2M ammonia in MeOH solution in $CH_2Cl_2$ to give the title compound (35.6 mg, 16%).

EXAMPLE 28

Synthesis of Compound 4(a)

Azalide derivative h, shown in Scheme 3 and prepared according to Scheme 1 and Examples 1–12 above, wherein $R^{15}$ is methyl (0.528 g, 0.667 mmol) was dissolved in THF (50 mL), and the resultant solution was cooled to 0° C. Under stirring conditions, NBS (0.119 g, 0.670 mmol) was added and the stirring was continued at 0° C. for 0.5 hour. EtOAc (250 mL) was added, and the organic layer was washed with 0.1 N NaOH solution (50 mL), and brine (50 mL). The organic layer was then dried with $Na_2SO_4$, and the solvent was removed in vacuo to give the crude product which was purified by flash chromatography using 3% 2 M ammonia in MeOH solution in $CH_2Cl_2$ to give the title compound (275 mg, 52%).

EXAMPLE 29

Synthesis of Compound 4(b)

Azalide derivative h, shown in Scheme 3, wherein $R^{15}$ is vinyl, (85.1 mg, 0.106 mmol) was dissolved in THF (10 mL), and the resultant solution was cooled to 0° C. Under stirring conditions was added NBS (19.7 mg, 0.111 mmol), and the stirring was continued at 0° C. for 2 hours. EtOAc (100 mL) was added, and the organic layer was washed with 0.3 N NaOH solution (10 mL), and brine (10 mL). The organic layer was then dried with $Na_2SO_4$, and the solvent was removed in vacuo to give the crude product. The product was purified by flash chromatography first using 7% 2 M ammonia in MeOH solution in $CH_2Cl_2$ then 7% 2 M ammonia in MeOH solution in EtOAc (28.4 mg, 33%).

EXAMPLE 30

Synthesis of Compound 5(a)

Compound 5(a), wherein R2 is OH, $R^5$ is ethyl, $R^9$ is H, and $R^{10}$ is OH, was prepared according to Scheme 4:

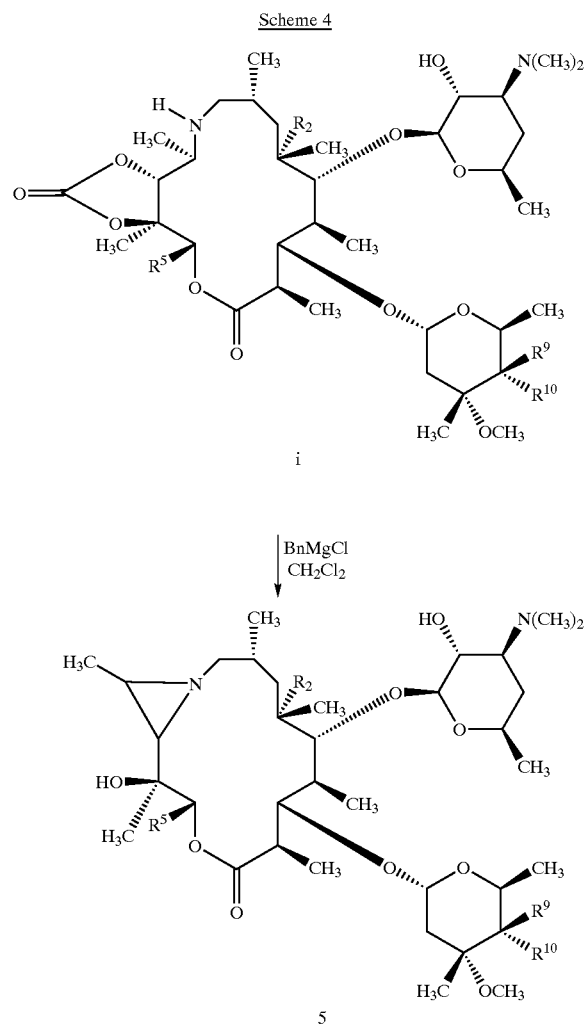

According to Scheme 4, compounds of Formula 5 can be prepared by reacting a compound of Formula i with a Grignard reagent such as benzylmagnesium chloride or a base such as isopropylcyclohexylamino magnesium chloride in a solvent such at dichloromethane at an appropriate temperature.

In particular, the azalide carbonate i wherein $R^2$ is OH, $R^5$ is ethyl, $R^9$ is H, and $R^{10}$ is OH, the synthesis of which is disclosed by U.S. provisional patent application No. 60/097075, which is incorporated herein by reference, (2.28 g, 3 mmol) was dissolved in $CH_2Cl_2$, under stirring conditions was added benzyl magnesium chloride (15.0 mL, 30 mmol) over 2 minutes. After the resulting reaction mixture was stirred at room temperature for 1 hour, it was quenched with saturated $NH_4Cl$ solution (50 mL). The product was extracted with $CH_2Cl_2$ (300 mL). The organic layer was then washed with brine (50 mL), dried with $Na_2SO_4$, and the solvent was removed in vacuo to give the crude product which was purified by flash chromatography using 1.25% MeOH, 0.5% ammonia in $CH_2Cl_2$ to give the title compound (851 mg, 40%, MS: 717.2).

EXAMPLE 31

Synthesis of Compound 6(a)

Compound 6(a) was prepared according to Scheme 5:

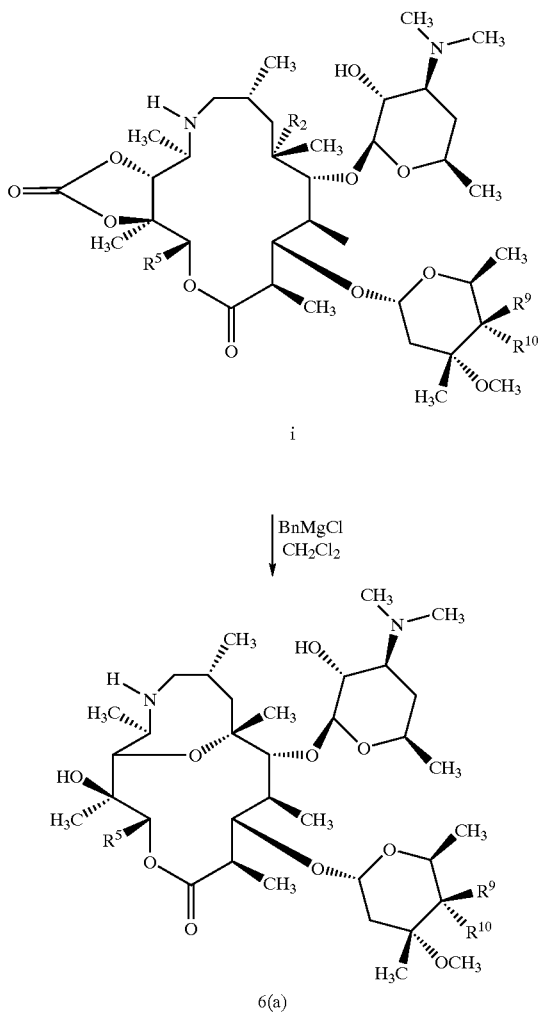

According to Scheme 5, compounds of Formula 6(a) can be prepared by reacting compounds of Formula i with a Grignard reagent such as vinyl magnesium bromide in a solvent such at dichloromethane at an appropriate temperature. Suitable reaction times are typically about 0.5 hour to about 24 hours.

In particular, azalide carbonate i (3.00 g, 3.95 mmol) was dissolved in $CH_2Cl_2$ (100 mL) and cooled to −78° C. Under stirring conditions was added vinyl magnesium bromide, and the stirring was continued at −78° C. for 1.5 hours. The reaction was then quenched with saturated $NH_4Cl$ solution (50 mL), and the reaction mixture was warmed to room temperature. The aqueous layer was extracted with $CH_2Cl_2$ (200 mL), and the combined organic layers were washed with saturated $NaHCO_3$ solution (50 mL), brine (50 mL). The organic layer was dried with $Na_2SO_4$, and the solvent was removed in vacuo to give the crude product which was purified by flash chromatography using 4% MeOH, 0.5% ammonia in $CH_2Cl_2$ to give example 5 as the major product (27%) and example 31 as the minor product (40.0 mg, 1.4%, MS: 717.2).

EXAMPLE 32

Synthesis of Compound 7(a)

As shown below in Scheme 6, acidic conditions can be used to remove the cladinose moiety of compounds of Formula 5, thereby forming compounds of Formula 7:

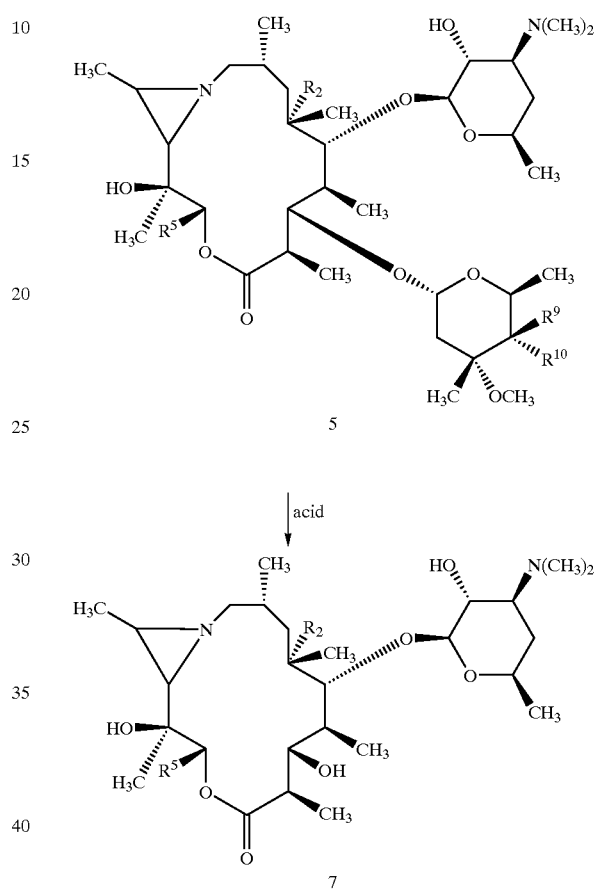

In this example, compound 7(a), which is of Formula 7 wherein $R^2$ is OH and $R^5$ is ethyl, was prepared by adding acetyl chloride (5.95 µL) to methanol (2 mL) in a 25 mL round bottomed flask. The resulting solution was stirred at room temperature for 5 minutes. Azalide derivative 5(a) (20.0 mg) was added to the solution, and the reaction mixture was stirred at room temperature for 48 hours. MeOH was then removed in vacuo, the residue was dissolved in methylene chloride (20 mL) and saturated sodium bicarbonate solution (10 mL). After separation, the organic layer was washed with brine (10 mL), dried with $MgSO_4$. The solvent was then removed in vacuo to give the crude product which was purified by flash chromatography using 5% MeOH and 1% ammonia in methylene chloride to give the title compound (14 mg, 89%, MS: 559.2).

EXAMPLE 33

Synthesis of Compound 8(a)

As shown below in Scheme 7, compounds such as 5(a) can be converted into compounds such as 8(a) using methods such as those disclosed by WO 98/09978, which is incorporated herein by reference:

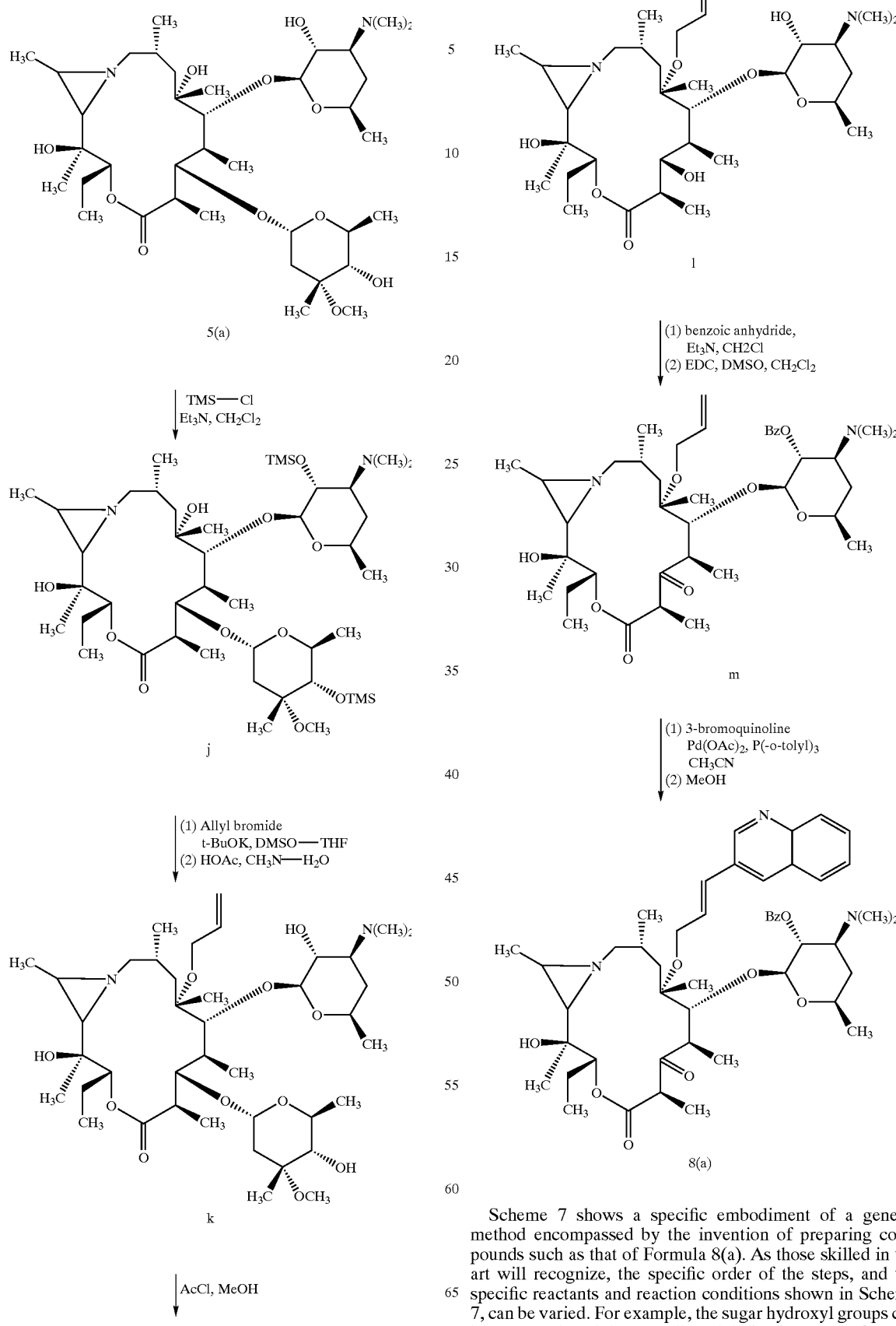

Scheme 7 shows a specific embodiment of a general method encompassed by the invention of preparing compounds such as that of Formula 8(a). As those skilled in the art will recognize, the specific order of the steps, and the specific reactants and reaction conditions shown in Scheme 7, can be varied. For example, the sugar hydroxyl groups can be protected, and the 6-O-alkenyl derivative can be formed, prior to cleavage of the cladinose moiety. However, in the preferred embodiment of the general synthetic method of the invention shown in Scheme 7, the 2'- and 4"-hydroxy groups of a compound such as that of Formula 5(a) are first protected by reaction with a suitable hydroxy protecting reagent such as TMS-Cl, acetic anhydride, or benzoic anhydride in an aprotic solvent such as dichloromethane to yield compound j.

The 6-hydroxy group of compound j is then alkylated by reaction with an alkylating agent in the presence of base, followed by the removal of the 2'- and 4"-hydroxy protecting groups to give compound k. Alkylating agents include, but are not limited to, alkyl chlorides, bromides, iodides or alkyl sulfonates. Specific examples of alkylating agents include, but are not limited to, allyl bromide, propargyl bromide, benzyl bromide, and allyl O-tosylate. Examples of solvents include, but are not limited to, aprotic solvents such as DMSO, DMF, THF, diethyl ether, and mixtures thereof. Examples of base which can be used to provide a compound of Formula k include, but are not limited to, potassium hydroxide, potassium isopropoxide, and potassium tert-butoxide. The deprotection of the 2'- and 4"-hydroxy groups is carried out by standard methods known to those skilled in the art.

Compound k is converted into compound l by removal of the cladinose moiety. Suitable reaction conditions include those described above in Example 31. The 2'-hydroxyl group of compound l is next protected by reaction with benzoic anhydride as in step 1. Depending on the compound, this reaction time can vary from about 1 hour to about 2 days. The 3-hydroxyl group of compound l is then oxidized to yield the ketone of compound m using a modified Swern oxidation procedure. Suitable oxidizing agents include, but are not limited to, carbodiimide-dimethylsulfoxide and N-chlorosuccinimide-dimethyl sulfide.

In the final step of the general method exemplified by Scheme 7, compound m is converted to the 6-O-(substituted alkenyl) derivative (e.g., Formula 8(a)) by reaction with an aryl halide, a substituted aryl halide, a heteroaryl halide, or substituted heteroaryl halide under Heck conditions with Pd(II) or Pd(0), phosphine, and amine or organic base. See, e.g.,*Organic Reactions,*27:345–390 (1982). The 2'-hydroxyl protecting group is then removed by standard methods to give the compound of Formula 8(a).

In a specific application of the synthesis of Scheme 7, azalide derivative 5a (1 mmol) is dissolved in methylene chloride, followed by the addition of triethylamine (2.2 mmol). The resultant reaction mixture is cooled in an ice-water bath, TMS-Cl (2.2 eq.) is slowly added, and the reaction mixture is stirred at room temperature overnight. After the reaction is complete, the reaction mixture is concentrated in vacuo, and the residue is dissolved in methylene chloride. The organic layer is washed with water, brine, and dried with MgSO$_4$. The solvent is evaporated in vacuo to give azalide derivative j.

To a 0° C. solution of compound j (1 mmol) in 5 mL of DMSO and 5 mL of THF is added freshly distilled allyl bromide (1.1 mmol). After approximately 5 minutes, a solution of potassium tert-butoxide (1 M, 1.1 mL) in 5 mL of DMSO and 5 mL of THF is added dropwise over 4 hours. The reaction mixture is taken up in ethyl acetate (200 mL) and washed with water and brine. The organic solvent is removed in vacuo to give the allyl derivative. This allyl derivative (1 mmol) is dissolved in 10 mL of CH$_3$CN and 5 mL of H$_2$O, followed by the addition of AcOH (5 eq), and the resultant solution is stirred at room temperature for 4 to 24 hours. After the reaction is complete, the reaction mixture is diluted with toluene (100 mL) and concentrated in vacuo, and the crude product is purified by flash chromatography using 3% MeOH and 0.5% ammonia in CH$_2$Cl$_2$ to give azalide derivative k.

AcCl (3 mmol) is added to MeOH (30 mL), and the resulting solution is stirred at room temperature for 15 minutes. After the reaction solution is cooled to 0° C., compound k (1 mmol) is added and the reaction mixture is stirred at room temperature for 48 hours. The solvent is removed in vacuo, and the residue is dissolved in CH$_2$Cl$_2$. After washed with saturated NaHCO$_3$ solution, brine, and dried with Na$_2$SO$_4$, the organic solvent is removed in vacuo to give the crude product which is purified by flash chromatography using 3% MeOH and 0.5% ammonia in CH$_2$Cl$_2$ to yield azalide derivative l.

To a solution of compound l (1 mmol) in CH$_2$Cl$_2$ (10 mL) is added benzoic anhydride (1 mmol) and Et$_3$N (1 mmol), and the resultant reaction mixture is stirred at room temperature for 1 to 2 days. The reaction mixture is diluted with CH$_2$Cl$_2$, and washed with saturated NaHCO$_3$ solution, brine, and dried with Na$_2$SO$_4$, the organic solvent is removed in vacuo to give the benzoylated derivative. This is then dissolved in 20 mL of CH$_2$Cl$_2$, followed by the addition of DMSO (10 mmol). The reaction mixture is then cooled to 0° C., and EDC (4 mmol) is added. The reaction solution is stirred at room temperature overnight. After the reaction is complete, the reaction mixture is diluted with 100 mL of CH$_2$Cl$_2$, washed with saturated NaHCO$_3$ solution, brine, and dried with Na$_2$SO$_4$. The organic solvent is removed in vacuo to give the crude product which is purified by silica gel chromatography using 30% acetone in hexanes to afford azalide derivative m.

A mixture of compound m (0.25 mmol), palladium(II) acetate (0.2 eq), tri-o-tolylphosphine (0.4 eq), 3-bromoquinoline (2 eq), and triethylamine (2 eq) in 2 mL of acetonitrile is cooled to −78° C., degassed, and sealed. The reaction mixture is then warmed to 50° C. for 2 hours and stirred at 80° C. for 16 hours. The reaction mixture was taken up in CH$_2$Cl$_2$, washed with saturated NaHCO$_3$ solution, brine, and dried with Na$_2$SO$_4$, the organic solvent is removed in vacuo to give the crude product which is purified by silica gel chromatography using 2% MeOH in CH$_2$Cl$_2$. This purified product is then dissolved in MeOH, and the resultant solution is stirred at reflux for 6 to 24 hours. The solvent is then removed in vacuo, and the crude product is purified by flash chromatography using 2% MeOH and 0.5% ammonia in CH$_2$Cl$_2$ to give compound 8(a).

What is claimed is:

1. A method of preparing a compound of Formula 2

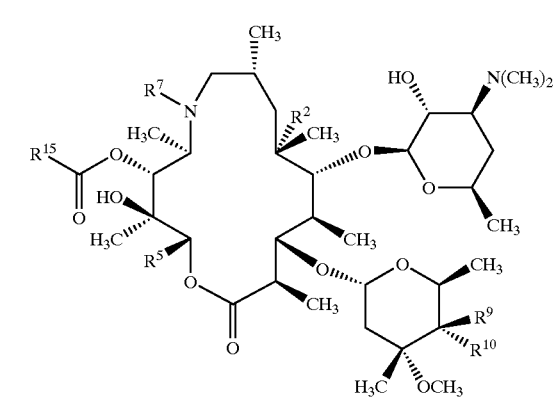

wherein $R^2$ is $-OR^{13}$ or $R^2$ with one H of the $-NR^7CH_2$-group can be taken together to form the moiety of Formula d;

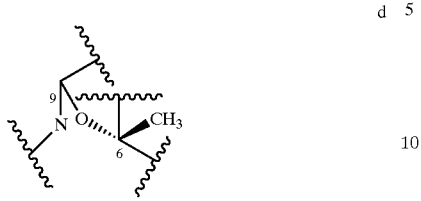

$R^5$ is an alpha-branched $C_2$–$C_8$ alkyl, $C_2$–$C_8$ alkenyl, $C_2$–$C_8$ alkynyl, $C_2$–$C_8$ alkoxyalkyl, or $C_2$–$C_8$ alkylthioalkyl group optionally substituted with at least one hydroxyl group; an alpha-branched $C_2$–$C_5$ alkyl group attached to a $C_5$–$C_8$ cycloalkyl group; a $C_3$–$C_8$ cycloalkyl or cycloalkenyl group optionally substituted with at least one moiety selected from the group consisting of methyl, hydroxyl, halo, and $C_1$–$C_4$ alkyl groups; or a 3–6 membered saturated, or fully or partially unsaturated, heterocycle comprising at least one atom of oxygen or sulphur and optionally substituted with one or more $C_1$–$C_4$ alkyl groups or halogen atoms;

$R^7$ is selected from the group consisting of H, $C_1$–$C_{10}$ alkyl, $C_2$–$C_{10}$ alkenyl, $C_2$–$C_{10}$ alkynyl, $-(CH_2)_m(C_6$–$C_{10}$ aryl), and $-(CH_2)_m$(5–10 membered heteroaryl), wherein the alkyl, alkenyl, aryl, heteroaryl, and alkynyl moieties of the foregoing $R^7$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl;

$R^9$ is hydroxy;

$R^{10}$ is selected from the group consisting of H, $C_1$–$C_{10}$ alkyl, $C_2$–$C_{10}$ alkenyl, $C_2$–$C_{10}$ alkynyl, cyano, $-CH_2S(O)_nR^{11}$, $-CH_2OR^{11}$, $-CH_2NR^{11}R^{12}$, $-(CH_2)_m(C_6$–$C_8$ aryl), and $-(CH_2)_m$(5–10 membered heteroaryl), wherein the alkyl, alkenyl, alkynyl, aryl, and heteroaryl moieties of the foregoing $R^{10}$ groups are optionally substituted with 1 to 3 substituents independently selected from the group consisting of halo cyano nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl;

each $R_{11}$ and $R_{12}$ is independently selected from the group consisting of H, $C_1$–$C_6$ alkyl, $C_2$–$C_6$ alkenyl, $(CH_2)_m(C_6$–$C_{10}$ aryl), $(CH_2)_m$(5–10 membered heteroaryl), and $C_2$–$C_{10}$ alkynyl, wherein the alkyl, alkenyl, aryl, heteroaryl, and alkynyl moieties of the foregoing $R^{11}$ and $R^{12}$ groups are optionally substituted with 1 to 3 substituents independently selected from the group consisting of halo, cyano, nitro, trifluoromethyl, $C_1$–$C_6$ alkyl, and $C_1$–$C_6$ alkoxy;

$R^{13}$ is selected from the group consisting of H, $C_1$–$C_{10}$ alkyl, $C_2$–$C_{10}$ alkenyl, $C_2$–$C_{10}$ alkynyl, $-R^{16}(C_6$–$C_{10}$ aryl), and $-R^{16}$(5–10 membered heteroaryl), wherein the alkyl, alkenyl, alkynyl, aryl, and heteroaryl moieties of the foregoing $R^{13}$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_1$–$C_{10}$ aryl, and 5–10 membered heteroaryl:

$R^{14}$ is selected from the group consisting of $C_1$–$C_{10}$ alkyl, $C_2$–$C_{10}$ alkenyl, $C_2$–$C_{10}$ alkynyl, $-(CH_2)_m(C_6$–$C_{10}$ aryl), and $-(CH_2)_m$(5–10 membered heteroaryl), wherein the alkyl, alkenyl, aryl, heteroaryl, and alkynyl moieties of the foregoing $R^{14}$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^{15}$ is independently selected from the group consisting of H, $C_1$–$C_{10}$ alkyl, $C_2$–$C_{10}$-alkenyl, $C_2$–$C_{10}$ alkynyl, $-(CH_2)_m(C_6$–$C_{10}$ aryl), and $-(CH_2)_m$(5–10 membered heteroaryl), wherein the alkyl alkenyl, alkynyl, aryl, and heteroaryl moieties of the foregoing $R^{15}$ groups are optionally substituted with 1 to 3 substituents independently selected from the group consisting of halo cyano nitro, trifluoromethyl, azido, $-C(O)R^{11}$, $-OC(O)R^{11}$, $-NR^{11}C(O)R^{12}$, $-C(O)NR^{11}R^{12}$, $NR^{11}R^{12}$ hydroxy, $C_1$–$C_6$ alkyl, $C_1$–$C_6$ alkoxy, $C_6$–$C_{10}$ aryl, and 5–10 membered heteroaryl;

$R^{16}$ is selected from the group consisting of $C_1$–$C_6$ alkyl, $C_3$–$C_6$ alkenyl, and $C_3$–$C_6$ alkynyl, wherein the alkyl, alkenyl, and alkynyl moieties of the foregoing $R^{16}$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl, and wherein at least one carbon atom of each of the foregoing $R^{16}$ groups can optionally be replaced with 1 to 3 atoms or moieties independently selected from group consisting of O, $N(R^{15})$, and S;

each n independently represents an integer of from 0 to 2; and each m independently represents an integer of from 0 to 4, which comprises contacting a compound of Formula f

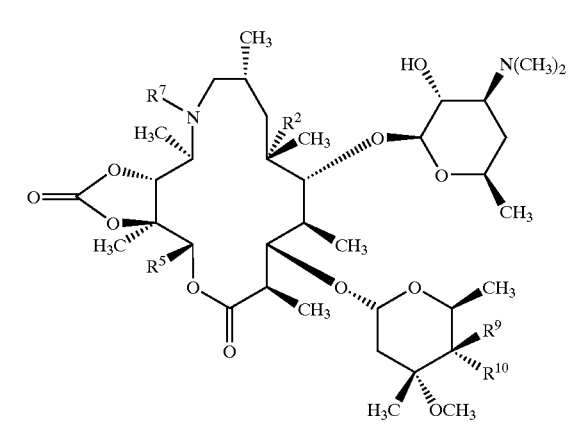

with a Grignard reagent for a time and at a temperature sufficient to form a compound of Formula 2.

2. A method of preparing a compound of Formula 4

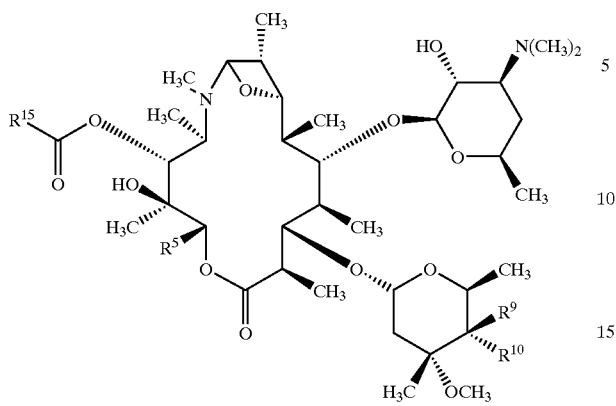

wherein $R^5$ is an alpha-branched $C_2$–$C_8$ alkyl, $C_2$–$C_8$ alkenyl, $C_2$–$C_8$ alkynyl, $C_2$–$C_8$ alkoxyalkyl, or $C_2$–$C_8$ alkylthioalkyl group optionally substituted with at least one hydroxyl group; an alpha-branched $C_2$–$C_5$ alkyl group attached to a $C_5$–$C_8$ cycloalkyl group; a $C_3$–$C_8$ cycloalkyl or cycloalkenyl group optionally substituted with at least one moiety selected from the group consisting of methyl, hydroxyl, halo, and $C_1$–$C_4$ alkyl groups; or a 3–6 membered saturated, or fully or partially unsaturated, heterocycle comprising at least one atom of oxygen or sulphur and optionally substituted with one or more $C_1$–$C_4$ alkyl groups or halogen atoms;

$R^9$ is hydroxy;

$R^{10}$ is selected from the group consisting of H, $C_1$–$C_{10}$ alkyl, $C_2$–$C_{10}$ alkenyl, $C_2$–$C_{10}$ alkynyl, cyano, —$CH_2S(O)_n{}^{11}$, —$CH_2OR^{11}$, —$CH_2NR^{11}R^{12}$, —$(CH_2)_m(C_6$–$C_8$ aryl), and —$(CH_2)_m$(5–10 membered heteroaryl), wherein the alkyl, alkenyl, alkynyl, aryl, and heteroaryl moieties of the foregoing $R^{10}$ groups are optionally substituted with 1 to 3 substituents independently selected from the group consisting of halo, cyano, nitro, trifluoromethyl, azido, —$C(O)R^{11}$, —$OC(O)R^{11}$, —$NR^{11}C(O)R^{12}$, —$C(O)NR^{11}R^{12}$, —$NR^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^{11}$ and $R^{12}$ is independently selected from the group consisting of H, $C_1$–$C_6$ alkyl, $C_2$–$C_6$ alkenyl, $(CH_2)_m(C_6$–$C_{10}$ aryl), $(CH_2)_m$(5–10 membered heteroaryl) and $C_2$–$C_{10}$ alkynyl, wherein the alkyl, alkenyl, aryl, heteroaryl, and alkynyl moieties of the foregoing $R^{11}$ and $R^{12}$ groups are optionally substituted with 1 to 3 substituents independently selected from the group consisting of halo, cyano, nitro, trifluoromethyl, $C_1$–$C_6$ alkyl, and $C_1$–$C_6$ alkoxy;

$R^{13}$ is selected from the group consisting of H, $C_1$–$C_{10}$ alkyl, $C_2$–$C_{10}$ alkenyl, $C_2$–$C_{10}$ alkynyl, —$R^{16}(C_6$–$C_{10}$ aryl), and —$R^{16}$(5–10 membered heteroaryl), wherein the alkyl, alkenyl, alkynyl, aryl, and heteroaryl moieties of the foregoing $R^{13}$ groups are optionally substituted with 1 to 3 substituents independently selected from the grout consisting of halo, cyano, nitro, trifluoromethyl, azido, —$C(O)R^{11}$, —$OC(O)R^{11}$, —$NR^{11}C(O)R^{12}$, —$C(O)NR^{11}R^{12}$, —$NR^{11}R^{12}$, hydroxy, $C_1$–$C_6$ alkyl, $C_1$–$C_6$ alkoxy, $C_6$–$C_{10}$ aryl, and 5–10 membered heteroaryl;

$R^{14}$ is selected from the group consisting of $C_1$–$C_{10}$ alkyl, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein the alkyl, alkenyl, aryl, heteroaryl, and alkynyl moieties of the foregoing $R^{14}$ groups are optionally substituted with 1 to 3 substituents independently selected from the group consisting of halo cyano nitro, trifluoromethyl azido, —$C(O)R^{11}$, —$OC(O)R^{11}$, —$NR^{11}C(O)R^{12}$, —$C(O)NR^{11}R^{12}$, $NR^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^{15}$ is independently selected from the group consisting of H, $C_1$–$C_{10}$ alkyl, $C_2$–$C_{10}$-alkenyl, $C_2$–$C_{10}$ alkynyl, —$(CH_2)_m(C_6$–$C_{10}$ aryl), and —$(CH_2)_m$(5–10 membered heteroaryl), wherein the alkyl, alkenyl, alkynyl, aryl, and heteroaryl moieties of the foregoing $R^{15}$ groups are optionally substituted with 1 to 3 substituents independently selected from the group consisting of halo cyano nitro, trifluoromethyl, azido, —$C(O)R^{11}$, —$OC(O)R^{11}$, —$NR^{11}C(O)R^{12}$, —$C(O)NR^{11}R^{12}$, —$NR^{11}R^{12}$, hydroxy, $C_1$–$C_6$ alkyl, $C_1$–$C_6$ alkoxy, $C_2$–$C_{10}$ aryl, and 5–10 membered heteroaryls;

$R^{16}$ is selected from the group consisting of C1 C6 alkyl, C3 C6 alkenyl, and C3 C6 alkynyl, wherein the alkyl, alkenyl, and alkynyl moieties of the foregoing R16 groups are optionally substituted with 1 to 3 substituents independently selected from the group consisting of halo, cyano, nitro, trifluoromethyl, azido, C(O)R11, OC(O)R11, NR11C(O)R12, C(O)NR11R12, NR11R12, hydroxy, C1 C6 alkyl, C1 C6 alkoxy, C6 C10 aryl, and 5 10 membered heteroaryl, and wherein at least one carbon atom of each of the foregoing R16 groups can optionally be replaced with 1 to 3 atoms or moieties independently selected from group consisting of O, N(R15), and S;

which comprises contacting a compound of Formula h h

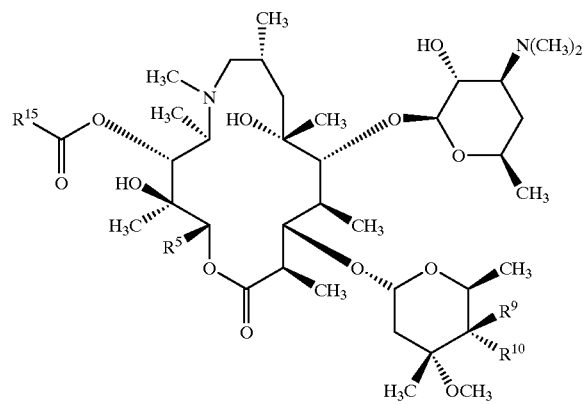

with an amine oxidizing reagent for a time and at a temperature sufficient to form a compound of Formula 4.

3. The method of claim 2 wherein the amine oxidizing reagent is selected from the group consisting of N-bromosuccinimide, N-chlorosuccinimide, iodine, and bromine.

4. A method of preparing a compound of Formula 5

5

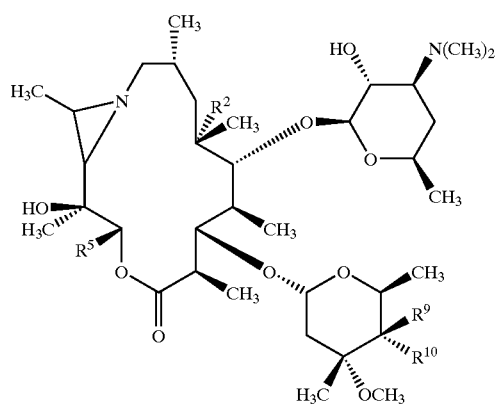

wherein $R^2$ is $—OR^{13}$ or $R^2$ with one H of the $—NCH_2$-group can be taken together to form the moiety of Formula d;

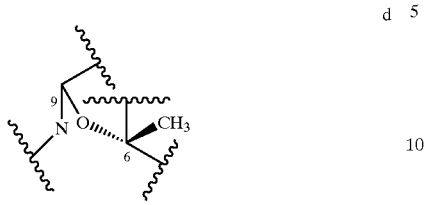

$R^5$ is an alpha-branched $C_2-C_8$ alkyl, $C_2-C_8$ alkenyl, $C_2-C_8$ alkynyl, $C_2-C_8$ alkoxyalkyl, or $C_2-C_8$ alkylthioalkyl group optionally substituted with at least one hydroxyl group; an alpha-branched $C_2-C_5$ alkyl group attached to a $C_5-C_8$ cycloalkyl group; a $C_3-C_8$ cycloalkyl or cycloalkenyl group optionally substituted with at least one moiety selected from the group consisting of methyl, hydroxyl, halo, and $C_1-C_4$ alkyl groups; or a 3–6 membered saturated, or fully or partially unsaturated, heterocycle comprising at least one atom of oxygen or sulphur and optionally substituted with one or more $C_1-C_4$ alkyl groups or halogen atoms;

$R^7$ is selected from the group consisting of H, $C_1-C_{10}$ alkyl, $C_2-C_{10}$ alkenyl, $C_2-C_{10}$ alkynyl, $—(CH_2)_m(C_6-C_{10}$ aryl), and $—(CH_2)_m$(5–10 membered heteroaryl), wherein the alkyl, alkenyl, aryl, heteroaryl, and alkynyl moieties of the foregoing $R_7$ groups are optionally substituted with 1 to 3 substituents independently selected from the group consisting of halo, cyano, nitro, trifluoromethyl, azido, $—C(O)R^{11}$, $—OC(O)R^{11}$, $—NR^{11}C(O)R^{12}$, $—C(O)NR^{11}R^{12}$, $—NR_{11}R_{12}$, hydroxy, $C_1-C_6$ alkyl, $C_1-C_{10}$ alkoxy, $C_6-C_{10}$ aryl, and 5–10 membered heteroaryl;

$R^9$ is hydroxy;

$R^{10}$ is selected from the group consisting of H, $C_1-C_{10}$ alkyl, $C_2-C_{10}$ alkenyl, $C_2-C_{10}$ alkynyl, cyano, $—CH_2S(O)_nR^{11}$, $—CH_2OR^{11}$, $—CH_2NR^{11}R^{12}$, $—(CH_2)_m(C_6-C_8$ aryl), and $—(CH_2)_m$(5–10 membered heteroaryl), wherein the alkyl, alkenyl, alkynyl, aryl, and heteroaryl moieties of the foregoing $R^{10}$ groups are optionally substituted with 1 to 3 substituents independently selected from the group consisting of halo, cyano, nitro, trifluoromethyl, azido, $—C(O)R^{11}$, $—OC(O)R^{11}$, $—NR^{11}C(O)R^{12}$, $—C(O)NR^{11}R^{12}$—$NR^{11}R^{12}$, hydroxy, $C_1-C_6$ alkyl $C_1-C_6$ alkoxy, $C_6-C_{10}$ aryl, and 5–10 membered heteroaryl;

each $R^{11}$ and $R^{12}$ is independently selected from the group consisting of H, $C_1-C_6$ alkyl, $C_2-C_6$ alkenyl, $(CH_2)_m(C_6-C_{10}$ aryl), $(CH_2)_m$(5–10 membered heteroaryl), and alkynyl, wherein the alkyl, alkenyl, aryl, heteroaryl and alkynyl moieties of the foregoing $R^{11}$ and $R^{12}$ groups are optionally substituted with 1 to 3 substituents independently selected from the group consisting of halo, cyano, nitro, trifluoromethyl, $C_1-C_6$ alkyl, and $C_1-C_{10}$ alkoxy;

$R^{13}$ is selected from the group consisting of H, $C_1-C_{10}$ alkyl, $C_2-C_{10}$ alkenyl, $C_2-C_{10}$ alkynyl, $—R^{16}(C_6-C_{10}$ aryl), and $—R^{16}$(5–10 membered heteroaryl), wherein the alkyl, alkenyl, alkynyl, aryl, and heteroaryl moieties of the foregoing $R^{13}$ groups are optionally substituted with 1 to 3 substituents independently selected from the group consisting of halo, cyano, nitro, trifluoromethyl, azido, $—C(O)R^{11}$, $—OC(O)R_{11}$, $—NR_{11}C(O)R_{12}$, $—C(O)NR_{11}R_{12}$, $—NR_{11}R_{12}$, hydroxy, $C_1-C_6$ alkyl, $C_1-C_6$ alkoxy, $C_6-C_{10}$ aryl, and 5–10 membered heteroaryl;

$R^{14}$ is selected from the group consisting of $C_1-C_{10}$ alkyl, $C_2-C_{10}$ alkenyl, $C_2-C_{10}$ alkynyl, $—(CH_2)_m(C_6-C_{10}$ aryl), and $—(CH_2)_m$(5–10 membered heteroaryl), wherein the alkyl, alkenyl, aryl heteroaryl, and alkynyl moieties of the foregoing $R^{14}$ groups are optionally substituted with 1 to 3 substituents independently selected from the group consisting of halo cyano nitro, trifluoromethyl, azido, $—C(O)R^{11}$, $—OC(O)R^{11}$, $—NR^{11}C(O)R^{12}$, $—C(O)NR^{11}R^{12}$, $—NR^{11}R^{12}$, hydroxy, $C_1-C_6$ alkyl, $C_1-C_6$ alkoxy, $C_6-C_{10}$ aryl, and 5–10 membered heteroaryl;

each $R^{15}$ is independently selected from the group consisting of H, $C_1-C_{10}$ alkyl, $C_2-C_{10}$-alkenyl, $C_2-C_{10}$ alkynyl, $—(CH_2)_m(C_6-C_{10}$ aryl), and $—(CH_2)_m$(5–10 membered heteroaryl), wherein the alkyl, alkenyl, alkynyl, aryl, and heteroaryl moieties of the foregoing $R^{15}$ groups are optionally substituted with 1 to 3 substituents independently selected from the group consisting of halo cyano nitro, trifluoromethyl, azido, $—C(O)R^{11}$, $—OC(O)R^{11}$, $—NR^{11}C(O)R^{12}$, $—C(O)NR^{11}R_{12}$, $—NR^{11}R^{12}$, hydroxy, $C_1-C_6$ alkyl, $C_1-C_6$ alkoxy, $C_6-C_{10}$ aryl, and 5–10 membered heteroaryl;

$R^{16}$ is selected from the group consisting of $C_1-C_6$ alkyl, $C_3-C_6$ alkenyl, and $C_3-C_6$ alkynyl, wherein the alkyl, alkenyl, and alkynyl moieties of the foregoing $R^{16}$ groups are optionally substituted with 1 to 3 substituents independently selected from the group consisting of halo, cyano, nitro, trifluoromethyl, azido, $—C(O)R^{11}$, $—OC(O)R^{11}$, $—NR^{11}C(O)R^{12}$, $—C(O)NR^{11}R^{12}$, $—NR^{11}R^{12}$, hydroxy, $C_1-C_6$ alkyl, $C_1-C_6$ alkoxy, $C_6-C_{10}$ aryl, and 5–10 membered heteroaryl, and wherein at least one carbon atom of each of the foregoing $R^{16}$ groups can optionally be replaced with 1 to 3 atoms or moieties independently selected from group consisting of O, $N(R^{15})$, and S;

which comprises contacting a compound of Formula i

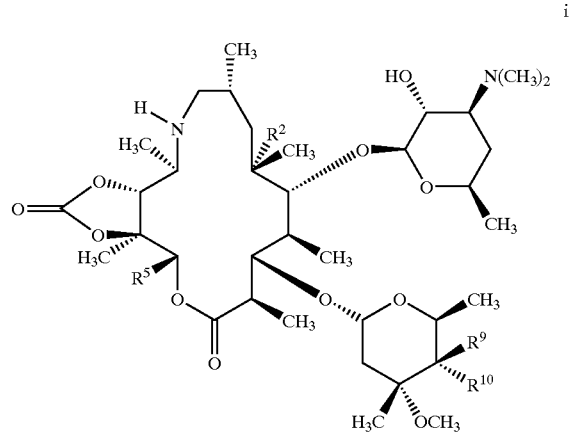

with a Grignard reagent or a base for a time and at a temperature sufficient to form a compound of Formula 5.

5. The method of claim 4 wherein the Grignard reagent is benzyl magnesium chloride or the base is isopropylcyclohexylamino magnesium chloride.

6. A method of forming a compound of Formula 7

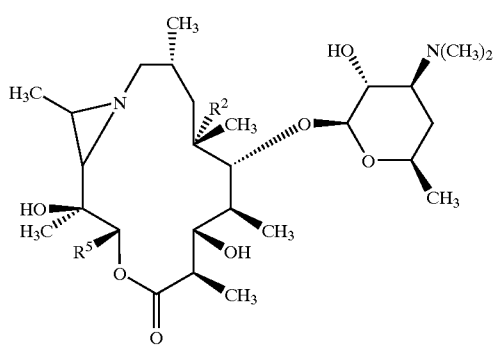

wherein $R^2$ is $-OR^{13}$
or $R^2$ with one H of the $-NR^7CH_2$-group can be taken together to form the moiety of Formula d;

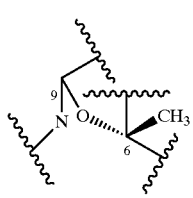

$R^5$ is an alpha-branched $C_2$–$C_8$ alkyl ($C_2$–$C_8$ alkenyl, ($C_2$–$C_8$ alkynyl, $C_2$–$C_8$ alkoxyalkyl, or ($C_2$–$C_8$ alkylthioalkyl group optionally substituted with at least one hydroxyl group; an alpha branched $C_2$–$C_5$ alkyl group attached to a $C_2$–$C_8$ cycloalkyl group, a $C_3$–$C_8$ cycloalkyl or cycloalkenyl group optionally substituted with at least one moiety selected from the group consisting of methyl, hydroxyl, halo, and $C_1$–$C_4$ alkyl groups; or a 3–6 membered saturated, or fully or partially unsaturated, heterocycle comprising at least one atom of oxygen or sulphur and optionally substituted with one or more $C_1$–$C_4$ alkyl groups or halogen atoms;

each $R^{11}$ and $R^{12}$ is independently selected from the group consisting of H, $C_1$–$C_6$ alkyl, $C_2$–$C_6$ alkenyl, $(CH_2)_m$($C_6$–$C_{10}$ aryl,$(CH_2)_m$(5–10 membered heteraryl), and $C_2$–$C_{10}$ alkynyl, wherein the alkyl, alkenyl, aryl, heteroaryl, and alkynyl moieties of the foregoing $R^{11}$ and $R^{12}$ groups are optionally substituted with 1 to 3 substituents independently selected from the group consisting of halo, cyano, nitro, trifluoromethyl, $C_1$–$C_6$ alkyl, and $C_1$–$C_6$ alkoxy;

$R^{13}$ is selected from the group consisting of H, $C_1$–$C_{10}$ alkyl, $C_2$–$C_{10}$ alkenyl, $C_2$–$C_{10}$ alkynyl, $-R^{16}(C_6$–$C_{10}$ aryl), and $-R^{16}$(5–10 membered heteroaryl), wherein the alkyl, alkenyl, alkynyl, aryl, and heteroaryl moieties of the foregoing $R^{13}$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl;

each $R^{15}$ is independently selected from the group consisting of H, $C_1$–$C_{10}$ alkyl, $C_2$–$C_{10}$-alkenyl, $C_2$–$C_{10}$ alkynyl, $-(CH_2)_m(C_6$–$C_{10}$ aryl), and $-(CH_2)_m$(5–10 membered heteroaryl), wherein the alkyl, alkenyl, alkynyl, aryl, and heteroaryl moieties of the foregoing $R^{15}$ groups are optionally substituted with 1 to 3 substituents independently selected from the group consisting of halo cyano nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$ hydroxy, $C_1$–$C_6$ alkyl, $C_1$–$C_6$ alkoxy, $C_6$–$C_{10}$ aryl, and 5–10 membered heteroaryl;

$R^{16}$ is selected from the group consisting of $C_1$–$C_6$ alkyl, $C_3$–$C_6$ alkenyl, and $C_3$–$C_6$ alkynyl, wherein the alkyl, alkenyl, and alkynyl moieties of the foregoing $R^{16}$ groups are optionally substituted with 1 to 3 substituents independently selected from the group consisting of halo, cyano, nitro, trifluoromethyl, azido, $-C(O)R^{11}$, $-OC(O)R^{11}$, $-NR^{11}C(O)R^{12}$, $-C(O)NR^{11}R^{12}$, $-NR^{11}R^{12}$, hydroxy, $C_1$–$C_6$ alkyl, $C_1$–$C_6$ alkoxy, $C_6$–$C_{10}$ aryl, and 5–10 membered heteroaryl, and wherein at least one carbon atom of each of the foregoing $R^{16}$ groups can optionally be replaced with 1 to 3 atoms or moieties independently selected from group consisting of O, $N(R^{15})$, and S;

each n independently represents an integer of from 0 to 2; and each m independently represents an integer of from 0 to 4, which comprises contacting a compound of Formula 5

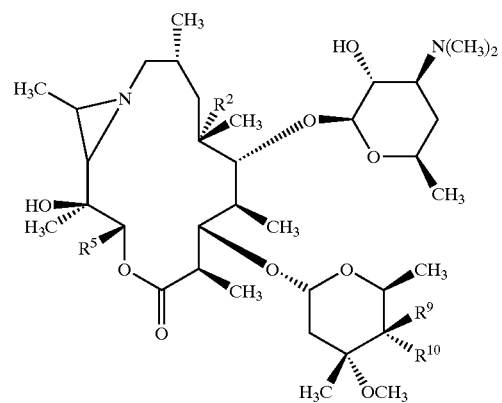

wherein $R^9$ and $R^{10}$ are defined herein, with acidic conditions for a time and at a temperature sufficient to form a compound of Formula 7.

* * * * *